(12) United States Patent
Rothbaum

(10) Patent No.: US 12,115,153 B2
(45) Date of Patent: Oct. 15, 2024

(54) METHODS OF TREATING CANCER

(71) Applicant: Kartos Therapeutics, Inc., New York, NY (US)

(72) Inventor: Wayne Rothbaum, Delray Beach, FL (US)

(73) Assignee: Kartos Therapeutics, Inc., New York, NY (US)

( * ) Notice: Subject to any disclaimer, the term of this patent is extended or adjusted under 35 U.S.C. 154(b) by 872 days.

(21) Appl. No.: 17/052,040

(22) PCT Filed: Apr. 30, 2019

(86) PCT No.: PCT/US2019/029906
§ 371 (c)(1),
(2) Date: Oct. 30, 2020

(87) PCT Pub. No.: WO2019/213074
PCT Pub. Date: Nov. 7, 2019

(65) Prior Publication Data
US 2021/0186946 A1 Jun. 24, 2021

Related U.S. Application Data

(60) Provisional application No. 62/834,848, filed on Apr. 16, 2019, provisional application No. 62/781,942, filed on Dec. 19, 2018, provisional application No. 62/701,088, filed on Jul. 20, 2018, provisional application No. 62/664,673, filed on Apr. 30, 2018.

(51) Int. Cl.
| *A61K 31/451* | (2006.01) |
| *A61K 9/00* | (2006.01) |
| *A61P 35/00* | (2006.01) |

(52) U.S. Cl.
CPC .......... *A61K 31/451* (2013.01); *A61K 9/0053* (2013.01); *A61P 35/00* (2018.01)

(58) Field of Classification Search
CPC .................................................. A61K 31/451
See application file for complete search history.

(56) References Cited

U.S. PATENT DOCUMENTS

| 8,952,036 | B2 | 2/2015 | Rew |
| 11,419,870 | B2 * | 8/2022 | Ferretti .............. A61K 31/4439 |
| 2014/0243372 | A1 | 8/2014 | Rew |
| 2016/0264526 | A1 | 9/2016 | Bio et al. |
| 2016/0279135 | A1 | 9/2016 | Lannutti et al. |
| 2016/0287569 | A1 | 10/2016 | Caenepeel et al. |
| 2016/0331751 | A1 | 11/2016 | Ferretti et al. |
| 2016/0339019 | A1 | 11/2016 | Aging et al. |

FOREIGN PATENT DOCUMENTS

| CN | 105358530 A | 2/2016 |
| CN | 105121407 A | 7/2017 |
| JP | 2016-510028 A | 1/2018 |

(Continued)

OTHER PUBLICATIONS

Mascarenhas J. et al., Open Label Phase I Study of Single Agent Oral RG7388 (idasanutlin) in Patients with Polycythemia Vera and Essential Thrombocythemia. Blood, Dec. 7, 2017, vol. 130, No. Supplement 1, p. 254.

(Continued)

*Primary Examiner* — Golam M Shameem
(74) *Attorney, Agent, or Firm* — Morgan, Lewis & Bockius LLP

(57) ABSTRACT

Therapeutic methods and pharmaceutical compositions for treating cancer including a myeloproliferative neoplasm (MPN), including polycythemia vera (PV), essential thrombocythemia (ET), and primary myelofibrosis in a human subject are described. In certain embodiments, the invention includes therapeutic methods of treating a MPN using a MDM2 inhibitor of Formula (I) or Formula (II).

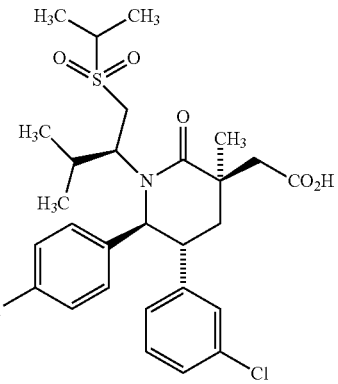

(I)

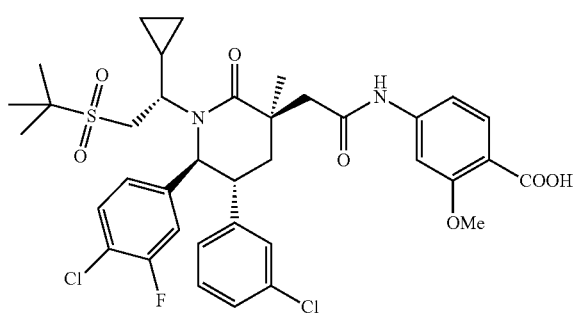

(II)

24 Claims, 10 Drawing Sheets

(56) References Cited

FOREIGN PATENT DOCUMENTS

| JP | 2016-504307 A | 12/2018 |
|---|---|---|
| JP | 2017-519019 A | 7/2020 |
| JP | 2016-528179 A | 2/2022 |
| TW | 201505630 A | 2/2015 |
| WO | 2011153509 A1 | 12/2011 |
| WO | 2015/198266 A1 | 12/2015 |

OTHER PUBLICATIONS

Arber D. A. et al., The 2016 revision to the World Health Organization classification of myeloid neoplasms and acute leukemia. Blood, May 19, 2016, vol. 127, No. 20, pp. 2391-2405 pp. 2392, 2397.
Search Report dated Jul. 31, 2022 for Singapore application No. 11202010793U, 3 pages.
Extended European Search Report dated Jan. 4, 2022 for European Patent Application No. 19796292, 8 pages.
Erba Harry P. et al: "Phase Ib study of the MDM2 inhibitor AMG 232 with or without trametinib in relapsed/refractory acute myeloid leukemia", Blood Advances, vol. 3, No. 13, Jun. 2, 2017, pp. 1939-1949.
Search Report dated Feb. 18, 2022 for Chilean application No. 202002833, 4 pages.
International Search Report and Written Opinion dated Aug. 5, 2019 for International Patent Application No. PCT/US2019/029906, 16 pages.
Gerds A. T., "Myeloproliferative Neoplasms", 2016, pp. 1-18; retrieved from the Internet: <http://www.clevelandclinicmeded.com/medicalpubs/diseasemanagement/hematology- oncology/chronic-myeloproliferative-disorders/>.
Gulen T. et al., "Systemic mastocytosis: progressive evolution of an occult disease into fatal mast cell leukemia: unique findings on an unusual hematological neoplasm", Medical Oncology, 2012 vol. 29, issue 5, pp. 3540-3546; retrieved from the Internet.
Talati C. et al., "An exercise in extrapolation: clinical management of atypical CML, MDS/MPN-unclassifiable, and MDS/MPN-RS-T", Current Hematologic Malignancy Reports, 2016, vol. 11, issue 6, pp. 425-433.
'Idasanutlin Well Tolerated in Patients With Polycythemia Vera and Essential Thrombocythemia', ASH Clinical News, Feb. 2, 2018, pp. 1-3.
International Preliminary Report on Patentability dated Nov. 3, 2020 for International Patent Application No. PCT/US2019/029906, 13 pages.
Erba, Harry Paul, et al, "Dose escalation results of a phase 1b study of the MDM2 inhibitor AMG 232 with or without trametinib in patients (Pts) with relapsed/refractory (r/r) acute myeloid leukemia (AML).", Journal of Clinical Oncology, 35, https://doi.org/10.1200/JCO.2017.35.15_suppl.7027, May 30, 2017 (May 30, 2017).
Zhao, Y., et al., "Small-Molecule Inhibitors of the MDM2-p53 Protein-Protein Interaction (MDM2 Inhibitors) in Clinical Trials for Cancer Treatment", Journal of Medicinal Chemistry, 58, pp. 1038-1052, https://dx.doi.org/10.1021/jm501092z, Nov. 14, 2014 (Nov. 14, 2014).

\* cited by examiner

METHODS OF TREATING CANCER

FIELD OF THE INVENTION

Methods of treating cancer including a myeloproliferative neoplasm (MPN) using a Mouse double minute 2 homolog (MDM2) inhibitor are disclosed herein.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, P14ARF. It has been suggested that alterations downstream of p53 may be responsible for at least partially inactivating the p53 pathway in p53 WT tumors (p53 wild type). In support of this concept, some p53WT tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are p53 WT, and studies with small molecule MDM2 inhibitors have yielded promising reductions in tumor growth both in vitro and in vivo. Further, in patients with p53-inactivated tumors, stabilization of wild type p53 in normal tissues by MDM2 inhibition might allow selective protection of normal tissues from mitotic poisons. As used herein, MDM2 means a human MDM2 protein and p53 means a human p53 protein. It is noted that human MDM2 can also be referred to as HDM2 or hMDM2. Several MDM2 inhibitors are in human clinical trials for the treatment of various cancers.

The myeloproliferative neoplasms (MPN), including but not limited to: polycythemia vera (PV), essential thrombocythemia (ET), and primary myelofibrosis (PMF), are clonal hematopoietic stem cell (HSC) disorders characterized by the clonal proliferation of terminally differentiated myeloid cells. Approximately 1%, 4%, and 20% of ET, PV and PMF patients, respectively, progress to a blast phase (BP) termed MPN-BP over a 10-year period from the time of diagnosis. Cervantes F, et al., *Acta Haematol.* 1991; 85(3):124-127. MPN-BP and de novo acute myeloid leukemia (AML) each have distinct mutational patterns and clinical courses. Rampal R, et al., *Proc Natl Acad Sci USA.* 2014; 111(50):E5401-10. Patients with MPN-BP have a particularly dismal prognosis with a median survival of less than 6 months with currently available therapies.

The present invention relates to methods of treating a myeloproliferative neoplasm in a human subject with an MDM2 inhibitor, alone or in combination with one or more additional pharmaceutically active agents.

The present invention relates to use of a MDM2 inhibitor, alone or in combination with one or more additional pharmaceutically active agents, for treating a myeloproliferative neoplasm (MPN).

SUMMARY OF THE INVENTION

The present invention relates to a method of treating a myeloproliferative neoplasm (MPN) comprising the step of administering to a human in need thereof a therapeutically effective amount of a MDM2 inhibitor, wherein the MDM2 inhibitor is a compound of Formula (I) or Formula (II):

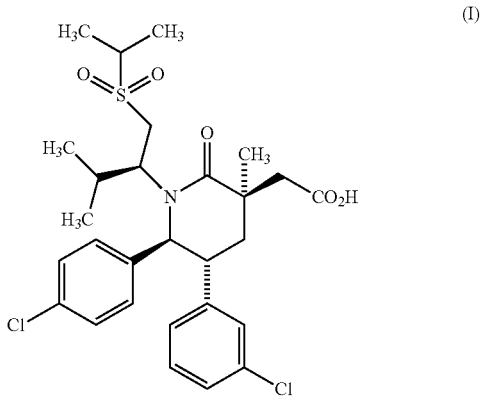

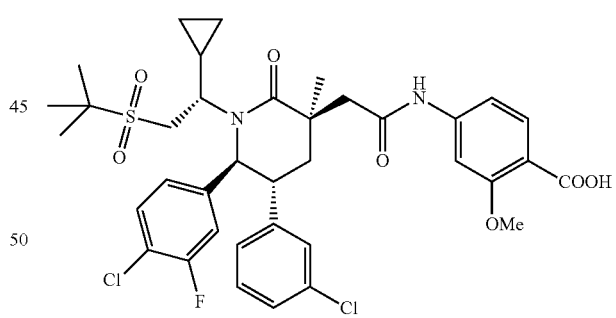

or a pharmaceutically acceptable salt thereof. In an embodiment, the MPN is selected from the group consisting of polycythemia vera (PV), myelofibrosis, primary myelofibrosis, thrombocythemia, essential thrombocythemia, idiopathic myelofibrosis, systemic mastocystosis (SM), chronic neutrophilic leukemia (CNL), myelodysplastic syndrome (MDS), and systemic mast cell disease (SMCD). In an embodiment, the MPN is selected from the group consisting of polycythemia vera (PV), primary myelofibrosis, and essential thrombocythemia. In an embodiment, the MPN is polycythemia vera (PV). In an embodiment, the MPN is essential thrombocythemia. In an embodiment, the MPN is myelofibrosis. In an embodiment, myelofibrosis is selected from primary myelofibrosis (PMF), post-polycythemia vera myelofibrosis (post-PV MF), and post-essential thrombocythemia myelofibrosis (post-ET MF). In an embodiment, the human subject failed Ruxolitinib therapy for any of the above MPN. In an embodiment, the human subject failed Ruxolitinib therapy for myelofibrosis. In an embodiment, the human subject failed Ruxolitinib therapy for primary myelofibrosis (PMF). In an embodiment, the human subject failed Ruxolitinib therapy for post-polycythemia vera myelofibrosis (post-PV In an embodiment, the human subject failed Ruxolitinib therapy for post-essential thrombocythemia myelofibrosis (post-ET MF).

In an embodiment, the present invention relates to a method of treating polycythemia vera (PV) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating essential thrombocythemia comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating primary myelofibrosis comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating idiopathic myelofibrosis comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating chronic myelogenous leukemia (CML) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating acute myelogenous leukemia (AML) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating Merkel cell carcinoma (MCC) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating systemic mastocystosis (SM) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating chronic neutrophilic leukemia (CNL) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating myelodysplastic syndrome (MDS) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, the present invention relates to a method of treating systemic mast cell disease (SMCD) comprising the step of administering to a human in need thereof a therapeutically effective amount of a MDM2 inhibitor, wherein the MDM2 inhibitor is a compound of Formula (I) or Formula (II) or a pharmaceutically acceptable salt thereof.

In an embodiment, thrombocythemia is essential thrombocythemia (ET).

In an embodiment, the compound of Formula (I) or Formula (II) is in a crystalline form. In an embodiment, the crystalline form is characterized by a powder X-ray diffraction pattern comprising at least three peaks at diffraction angle 2 theta degrees selected from a group consisting of peaks at approximately 11.6, 12.4, 18.6, 19.0, 21.6 and 23.6±0.1.

In an embodiment, the compound of Formula (I) or Formula (II) is in an amorphous form.

In an embodiment, the compound of Formula (I) or Formula (II) is in a free form.

In an embodiment, the MDM2 inhibitor is a pharmaceutically acceptable salt of a compound of Formula (I) or Formula (II).

In an embodiment, the compound of Formula (I) or Formula (II) is administered once daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

In an embodiment, the compound of Formula (I) or Formula (II) is administered twice daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

In an embodiment, the human is treated with the compound of Formula (I) for a period selected from the group consisting of about 14 days, about 21 days, about 28 days, about 35 days, about 42 days, about 49 days, and about 56 days.

In an embodiment, the compound of Formula (I) or Formula (II) is orally administered.

A MDM2 inhibitor for use in treating a myeloproliferative neoplasm (MPN) comprising the step of administering to a human in need thereof a therapeutically effective amount of the MDM2 inhibitor, wherein the MDM2 inhibitor is a compound of Formula (I) or Formula (II) or a pharmaceutically acceptable salt thereof.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

Figure 1:
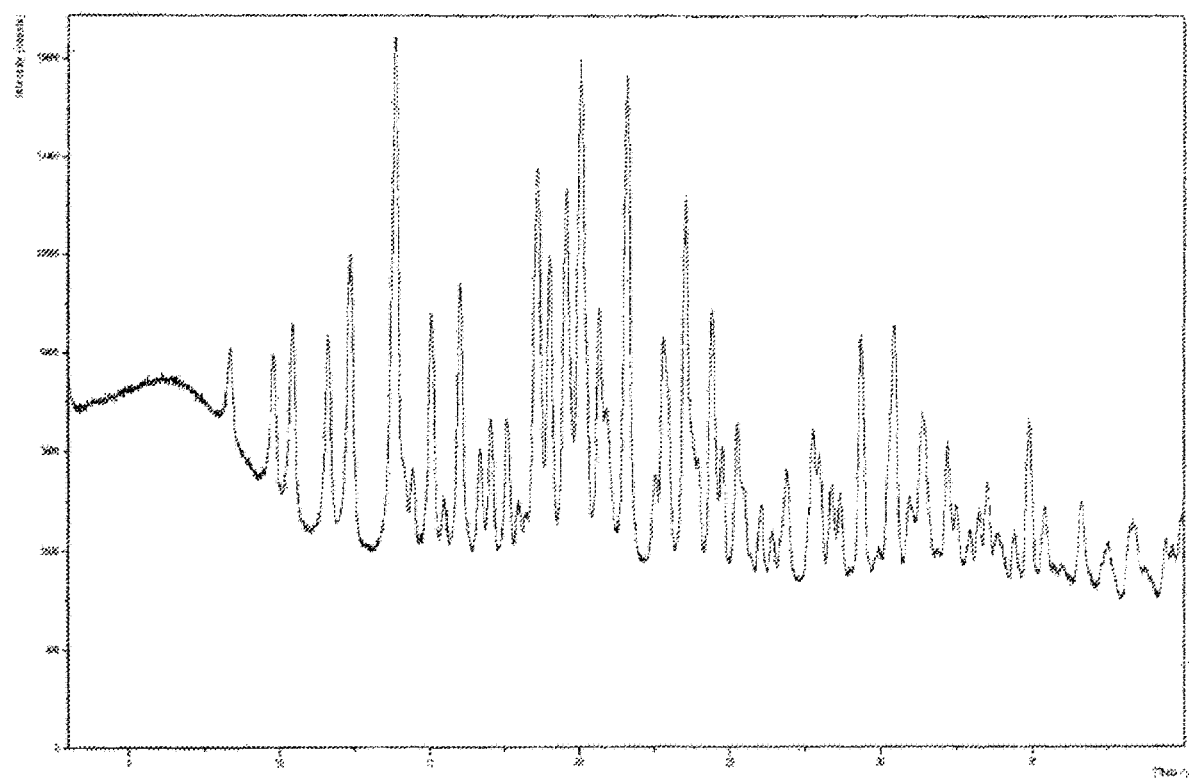
FIG. 1 illustrates XRPD pattern of the compound of Formula (I) in a crystalline anhydrous form.

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs.

The terms "administered in combination with" and "co-administration" as used herein, encompass administration of two or more active pharmaceutical ingredients to a subject so that both agents and/or their metabolites are present in the subject at the same time. Co-administration includes simultaneous administration in separate compositions, administration at different times in separate compositions, or administration in a composition in which two or more agents are present.

The term "effective amount" or "therapeutically effective amount" refers to that amount of an active pharmaceutical ingredient or combination of active pharmaceutical ingredients as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, and other factors which can readily be determined by one of ordinary skill in the art. The term also applies to a dose that will induce a particular response in target cells, (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "enantiomerically enriched," "enantiomerically pure," and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, such as at least 80% by weight. In some embodiments, the enrichment can be significantly greater than 80% by weight, providing a "substantially enantiomerically enriched," "substantially enantiomerically pure," or a "substantially non-racemic" preparation, which refers to preparations of compositions which have at least 85% by weight of one enantiomer relative to the other enantiomer, such as at least 90% by weight, and such as at least 95% by weight. The terms "diastereomerically enriched" and "diastereomerically pure," as used herein, refer to compositions in which the percent by weight of one diastereomer is greater than the amount of that one diastereomer in a control mixture of diastereomers. In some embodiments, the enrichment can be significantly greater than 80% by weight, providing a "substantially diastereomerically enriched" or "substantially diastereomerically pure" preparation, which refers to preparations of compositions which have at least 85% by weight of one diastereomer relative to other diastereomers, such as at least 90% by weight, and such as at least 95% by weight.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York (1981); E. L. Eliel and S. H. Wilen, *Stereochemistry of Organic Compounds*, Wiley-Interscience, New York (1994).

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

The term "$IC_{50}$" refers to the half maximal inhibitory concentration, i.e. inhibition of 50% of the desired activity. The term "$EC_{50}$" refers to the drug concentration at which one-half the maximum response is achieved.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"MPN-BP" refers to blast phase (BP) of the myeloproliferative neoplasms (MPN) described in this disclosure.

"Pharmaceutically acceptable carrier" or "pharmaceutically acceptable excipient" is intended to include any and all solvents, dispersion media, coatings, antibacterial and antifungal agents, isotonic, and absorption delaying agents. The use of such media and agents for active pharmaceutical ingredients is well known in the art. Except insofar as any conventional media or agent is incompatible with the active pharmaceutical ingredient, its use in the therapeutic compositions of the invention is contemplated. Supplementary active ingredients can also be incorporated into the described compositions.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve proton transfer between the cocrystal and the drug, and instead involves intermolecular interactions, such as hydrogen bonding, aromatic ring stacking, or dispersive forces, between the cocrystal former and the drug in the crystal structure.

The terms "QD," "qd," or "q.d." means quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

"Solvate" refers to a compound in physical association with one or more molecules of a pharmaceutically acceptable solvent.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds of the invention also include crystalline and amorphous forms of the compound of Formula (I) or Formula (II), including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Methods of Treating Cancer

The present invention relates to a method of treating cancer comprising the step of administering to a human in need thereof a Mouse double minute 2 homolog (MDM2) inhibitor, or a pharmaceutically acceptable salt thereof, wherein the cancer is selected from the group consisting of carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, head and neck, and skin (including basal and squamous cell carcinoma, melanoma skin cancer, Merkel cell carcinoma, Kaposi Sarcoma, skin lymphomas); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma, glioblastoma, and schwannomas); and other tumors (including melanoma, seminoma, teratocarcinoma, osteosarcoma, xenoderoma pigmentosum, keratoctanthoma, and thyroid follicular cancer). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

The present invention also relates to a use of a Mouse double minute 2 homolog (MDM2) inhibitor, or a pharmaceutically acceptable salt thereof, for treating cancer in a human in need thereof, wherein the cancer is selected from the group consisting of carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, head and neck, and skin (including basal and squamous cell carcinoma, melanoma skin cancer, Merkel cell carcinoma, Kaposi Sarcoma, skin lymphomas); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma, glioblastoma, and schwannomas); and other tumors (including melanoma, seminoma, teratocarcinoma, osteosarcoma, xenoderoma pigmentosum, keratoctanthoma, and thyroid follicular cancer). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

Methods of Treating a Myeloproliferative Neoplasm (MPN)

The present invention also relates to a method of treating a MPN comprising the step of administering to a human in need thereof a Mouse double minute 2 homolog (MDM2) inhibitor, or a pharmaceutically acceptable salt thereof. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T). In an embodiment, the polycythemia vera is phlebotomy-dependent polycythemia vera. In an embodiment, the human is determined as hydroxyurea (HU) intolerance (unacceptable side effects). In an embodiment, the human subject is determined as hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human failed Ruxolitinib therapy. Failed Ruxolitinib therapy includes, but is not limited to, (i) the absence of a reduction in the severity or progression of any MPN in a human subject receiving Ruxolitinib, or (ii) a relapse of any MPN in a human subject following Ruxolitinb therapy. In an embodiment, failed Ruxolitinib therapy is the absence of a reduction in the severity or progression of any MPN in a human subject receiving Ruxolitinib. In an embodiment, failed Ruxolitinib therapy is a relapse of any MPN in a human subject following Ruxolitinb therapy. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the present invention relates to a method of treating a MPN comprising the step of administering to a human in need thereof a Mouse double minute 2 homolog (MDM2) inhibitor, wherein the MDM2 inhibitor is a compound of Formula (I) or Formula (II) or a pharmaceutically acceptable salt thereof, wherein the MPN is selected from the group consisting of polycythemia vera (PV), myelofibrosis, and essential thrombocythemia (ET). In an embodiment, the polycythemia vera is phlebotomy-dependent polycythemia vera. In an embodiment, the human subject is determined as hydroxyurea (HU) intolerance (unacceptable side effects). In an embodiment, the human subject is determined as hydroxyurea (HU) resistant (inadequate response). In an embodiment, the human subject has splenomegaly. In an embodiment, the human has splenomegaly and is phlebotomy-dependent. In an embodiment, the human subject is phlebotomy-dependent without splenomegaly. In an embodiment, the human subject has failed previous MPN therapy with Ruxolitinib.

The present invention also relates to a method of treating a blast phase MPN (MPN-BP) comprising the step of administering to a human in need thereof a Mouse double minute 2 homolog (MDM2) inhibitor, or a pharmaceutically acceptable salt thereof. In an embodiment, the MPN-BP is selected from the group consisting of blast phase polycythemia vera (BP-PV), blast phase myelofibrosis, blast phase primary myelofibrosis, blast phase thrombocythemia, blast phase essential thrombocythemia (BP-ET), blast phase idiopathic myelofibrosis, blast phase systemic mastocystosis (BP-SM), blast phase chronic neutrophilic leukemia (BP-CNL), blast phase myelodysplastic syndrome (BP-MDS), and blast phase systemic mast cell disease (BP-SMCD). In an embodiment, the blast phase myelofibrosis is selected from the group consisting of blast phase primary myelofibrosis (BP-PMF), blast phase post-polycythemia vera myelofibrosis (BP-post-PV MF), and blast phase post-essential thrombocythemia myelofibrosis (BP-post-ET MF). In an embodiment, the blast phase primary myelofibrosis (BP-PMF) is selected from the group consisting of blast phase prefibrotic/early stage PMF and blast phase overt fibrotic stage PMF. In an embodiment, the MPN-BP is selected from the group consisting of blast phase chronic neutrophilic leukemia (BP-CNL), blast phase chronic eosinophilic leukemia, blast phase chronic myelomonocytic leukemia (BP-CMML), blast phase atypical chronic myeloid leukemia (BP-aCML), blast phase juvenile myelomonocytic leukemia (BP-JMML), blast phase hypereosinophilic syndromes (BP-HES), and blast phase myelodysplastic/myeloproliferative neoplasms with ring sideroblasts and thrombocytosis (BP-MDS/MPN-RS-T). In an embodiment, the blast phase polycythemia vera is phlebotomy-dependent polycythemia vera. In an embodiment, the human is determined as hydroxyurea (HU) intolerance (unacceptable side effects). In an embodiment, the human subject is determined as hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human failed Ruxolitinib therapy. Failed Ruxolitinib therapy includes, but is not limited to, (i) the absence of a reduction in the severity or progression of any MPN-BP in a human subject receiving Ruxolitinib, or (ii) a relapse of any MPN-BP in a human subject following Ruxolitinb therapy. In an embodiment, failed Ruxolitinib therapy is the absence of a reduction in the severity or progression of any MPN-BP in a human subject receiving Ruxolitinib. In an embodiment, failed Ruxolitinib therapy is a relapse of any MPN-BP in a human subject following Ruxolitinb therapy. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

In an embodiment, myelofibrosis is selected from primary myelofibrosis (PMF), post-polycythemia vera myelofibrosis (post-PV MF), and post-essential thrombocythemia myelofibrosis (post-ET MF).

In an embodiment, the myelofibrosis is selected from primary myelofibrosis (PMF), post-polycythemia vera myelofibrosis (post-PV MF), and post-essential thrombocythemia myelofibrosis (post-ET MF), and the human subject failed Ruxolitinib therapy for PMF, post-PV MF or post ET MF.

In an embodiment, the MPN is characterized by CALR mutation (calreticulin, located on chromosome 19p13.2), as described in Massie, et al., N Engl J. Med. 2013, 25: 2379-2390 and incorporated by reference herein in its entirety.

In an embodiment, the MPN is characterized by MPL mutation (myeloproliferative leukemia virus oncogene; located on chromosome 1p34), as described in Pikman, et al., Plos Med. 2006; 3(7):e270 and incorporated by reference herein in its entirety.

In an embodiment, the MPN is characterized by JAK2V617F mutation. JAK2V617F is a function mutation promoting cytokine-independent growth of myeloid cells and accounts for a majority of myeloproliferative neoplasms (MPN), as described in Nakatake et al (Oncogene, 2012, 31, 1323-1333) and incorporated by reference herein in its entirety.

In an embodiment, the MPN is characterized by one or more mutations selected from the group consisting of JAK2V617F, MPL, CALR, and mixtures thereof.

In an embodiment, the invention relates to a method of treating polycythemia vera (PV) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating polycythemia vera (PV) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin- 3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating polycythemia vera (PV) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating essential thrombocythemia (ET) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating essential thrombocythemia (ET) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating essential thrombocythemia (ET) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating primary myelofibrosis in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating primary myelofibrosis in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating primary myelofibrosis in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating post-polycythemia vera myelofibrosis (post-PV MF) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating post-polycythemia vera myelofibrosis (post-PV MF) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating post-polycythemia vera myelofibrosis (post-PV MF) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating post-essential thrombocythemia myelofibrosis (post-ET MF) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating post-essential thrombocythemia myelofibrosis (post-ET MF) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating post-essential thrombocythemia myelofibrosis (post-ET MF) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating chronic neutrophilic leukemia (CNL) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating chronic neutrophilic leukemia (CNL) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating chronic neutrophilic leukemia (CNL) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating chronic eosinophilic leukemia in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating chronic eosinophilic leukemia in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating chronic eosinophilic leukemia in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating chronic myelomonocytic leukemia (CMML) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating chronic myelomonocytic leukemia (CMML) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating chronic myelomonocytic leukemia (CMML) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating atypical chronic myeloid leukemia (aCML) in a human that comprises the step of administering to said human a therapeutically effective amount of a MDM2 inhibitor or a pharmaceutically acceptable salt thereof, wherein the MDM2 inhibitor is a compound of Formula (I) or Formula (II). In an embodiment, the invention relates to a method of treating atypical chronic myeloid leukemia (aCML) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating atypical chronic myeloid leukemia (aCML) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating juvenile myelomonocytic leukemia (JMML) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating juvenile myelomonocytic leukemia (JMML) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating juvenile myelomonocytic leukemia (JMML) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating hypereosinophilic syndromes (HES) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating hypereosinophilic syndromes (HES) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating hypereosinophilic syndromes (HES) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating myelodysplastic/myeloproliferative neoplasms with ring sideroblasts and thrombocytosis (MDS/MPN-RS-T) in a human that comprises the step of administering to said human a therapeutically effective amount of a MDM2 inhibitor or a pharmaceutically acceptable salt thereof, wherein the MDM2 inhibitor is a compound of Formula (I) or Formula (II).

In an embodiment, the invention relates to a method of treating myelodysplastic/myeloproliferative neoplasms with ring sideroblasts and thrombocytosis (MDS/MPN-RS-T) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the invention relates to a method of treating myelodysplastic/myeloproliferative neoplasms with ring sideroblasts and thrombocytosis (MDS/MPN-RS-T) in a human that comprises the step of administering to said human a therapeutically effective amount of a MDM2 inhibitor or a pharmaceutically acceptable salt thereof, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating a MPN in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a method of treating a MPN in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID, wherein the MPN is selected from the group consisting of polycythemia vera (PV), primary myelofibrosis, and essential thrombocythemia (ET).

In an embodiment, the invention relates to a method of treating a MPN in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID, wherein the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a method of treating polycythemia vera (PV) in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating primary myelofibrosis in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating post-polycythemia vera myelofibrosis (post-PV MF) in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating post-essential thrombocythemia myelofibrosis (post-ET MF) in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating essential thrombocythemia (ET) in a human that comprises the step of administering to said human a therapeutically effective amount of a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating a MPN in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a method of treating a MPN in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MPN is selected from the group consisting of polycythemia vera (PV), myelofibrosis, and essential thrombocythemia (ET). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a method of treating polycythemia vera (PV) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating primary myelofibrosis in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating post-polycythemia vera myelofibrosis (post-PV MF) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating post-essential thrombocythemia myelofibrosis (post-ET MF) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating essential thrombocythemia (ET) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating chronic neutrophilic leukemia (CNL) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating chronic eosinophilic leukemia in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating chronic myelomonocytic leukemia (CMML) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating atypical chronic myeloid leukemia (aCML) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating juvenile myelomonocytic leukemia (JMML) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating hypereosinophilic syndromes (HES) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating myelodysplastic/myeloproliferative neoplasms with ring sideroblasts and thrombocytosis (MDS/MPN-RS-T) in a human that comprises the step of administering to said human a therapeutically effective amount of a composition comprising a MDM2 inhibitor or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a use of a MDM2 inhibitor or a pharmaceutically acceptable salt thereof, in the manufacture of a medicament for treating a myeloproliferative neoplasm (MPN) comprises the step of administering to a human one or more doses of a MDM2 inhibitor or a pharmaceutically acceptable salt thereof. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a use of a MDM2 inhibitor or a pharmaceutically acceptable salt thereof, in the manufacture of a medicament for treating a myeloproliferative neoplasm (MPN) comprises the step of administering one or more doses of a MDM2 inhibitor or a pharmaceutically acceptable salt thereof, wherein the MPN is selected from the group consisting of polycythemia vera (PV), primary myelofibrosis, and essential thrombocythemia (ET).

In an embodiment, the invention relates to a use of a MDM2 inhibitor or a pharmaceutically acceptable salt thereof, in the manufacture of a medicament for treating polycythemia vera (PV), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating essential thrombocythemia (ET), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating primary myelofibrosis, wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating post-polycythemia vera myelofibrosis (post-PV MF), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating post-essential thrombocythemia myelofibrosis (post-ET MF), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating chronic neutrophilic leukemia (CNL), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating chronic eosinophilic leukemia, wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating chronic myelomonocytic leukemia (CMML), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating atypical chronic myeloid leukemia (aCML), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating juvenile myelomonocytic leukemia (JMML), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating hypereosinophilic syndromes (HES), wherein the treating comprises the step of administering to a human one or more doses of a MDM2 inhibitor or a pharmaceutically acceptable salt thereof.

In an embodiment, the invention relates to a use of a MDM2 inhibitor or a pharmaceutically acceptable salt thereof, in the manufacture of a medicament for treating myelodysplastic/myeloproliferative neoplasms with ring sideroblasts and thrombocytosis (MDS/MPN-RS-T), wherein the treating comprises the step of administering to a human one or more doses of a MDM2 inhibitor or a pharmaceutically acceptable salt thereof.

In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a use of a composition comprising a MDM2 inhibitor or a pharmaceutically acceptable salt thereof, in the manufacture of a medicament for treating a myeloproliferative neoplasm (MPN) comprises the step of administering to a human one or more doses of the composition comprising a MDM2 inhibitor or a pharmaceutically acceptable salt thereof. In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a use of a composition comprising a MDM2 inhibitor or a pharmaceutically acceptable salt thereof, in the manufacture of a medicament for treating a myeloproliferative neoplasm (MPN) comprises the step of administering to a human one or more doses of the composition comprising a MDM2 inhibitor or a pharmaceutically acceptable salt thereof, wherein the MPN is selected from the group consisting of polycythemia vera (PV), primary myelofibrosis, and essential thrombocythemia (ET). In an embodiment, the invention relates to a use of a composition comprising a MDM2 inhibitor or a pharmaceutically acceptable salt thereof, in the manufacture of a medicament for treating polycythemia vera (PV), wherein the treating comprises the step of administering to a human one or more doses of the composition comprising a MDM2 inhibitor or a pharmaceutically acceptable salt thereof. In an embodiment, the invention relates to a use of a composition comprising a MDM2 inhibitor or a pharmaceutically acceptable salt thereof, in the manufacture of a medicament for treating essential thrombocythemia (ET), wherein the treating comprises the step of administering to a human one or more doses of the composition comprising a MDM2 inhibitor or a pharmaceutically acceptable salt thereof. In an embodiment, the invention relates to a use of a composition comprising a MDM2 inhibitor or a pharmaceutically acceptable salt thereof, in the manufacture of a medicament for treating primary myelofibrosis, wherein the treating comprises the step of administering to a human one or more doses of the composition comprising a MDM2 inhibitor or a pharmaceutically acceptable salt thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a MDM2 inhibitor or a pharmaceutically acceptable salt thereof for use in treating a myeloproliferative neoplasm (MPN). In an embodiment, the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

In an embodiment, the invention relates to a MDM2 inhibitor or a pharmaceutically acceptable salt thereof for use in treating polycythemia vera (PV). In an embodiment, the invention relates to a MDM2 inhibitor or a pharmaceutically acceptable salt thereof for use in treating primary myelofibrosis. In an embodiment, the invention relates to a MDM2 inhibitor or a pharmaceutically acceptable salt thereof for use in treating essential thrombocythemia (ET).

In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

The methods described above may be used as first-line cancer therapy, or after treatment with conventional chemotherapic active pharmaceutical ingredients, including cyclophosphamide, fludarabine (FC chemotherapy), and chlorambucil.

In an embodiment, the invention relates to a method of treating a myelofibrosis selected from the group consisting of primary myelofibrosis (also known as chronic idiopathic myelofibrosis) and primary myelofibrosis secondary to polycythemia vera or essential thrombocythemia, comprising the step of administering a therapeutically effective amount of a MDM2 inhibitor or a pharmaceutically acceptable salt thereof.

In an embodiment, the invention relates to a method of treating a myelofibrosis selected from the group consisting of primary myelofibrosis (also known as chronic idiopathic myelofibrosis) and primary myelofibrosis secondary to polycythemia vera or essential thrombocythemia, comprising the step of administering a therapeutically effective amount of a composition comprising a MDM2 inhibitor or a pharmaceutically acceptable salt thereof.

In an embodiment, the invention relates to a method of treating a MPN in a human that comprises the step of administering to said human a therapeutically effective amount of a MDM2 inhibitor, or a pharmaceutically acceptable salt thereof, wherein the MPN is selected from the group consisting of polycythemia vera (PV), essential thrombocythemia (ET), and primary myelofibrosis, wherein the therapeutically effective amount is selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, and 480 mg QD. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating a MPN in a human that comprises the step of administering to said human a therapeutically effective amount of a MDM2 inhibitor, or a pharmaceutically acceptable salt thereof, wherein the MPN is selected from the group consisting of polycythemia vera (PV), essential thrombocythemia (ET), and primary myelofibrosis, wherein the therapeutically effective amount is 120 mg QD. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating a MPN in a human that comprises the step of administering to said human a therapeutically effective amount of a MDM2 inhibitor, or a pharmaceutically acceptable salt thereof, wherein the MPN is selected from the group consisting of polycythemia vera (PV), essential thrombocythemia (ET), and primary myelofibrosis, wherein the therapeutically effective amount is selected from the group consisting of 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the invention relates to a method of treating a MPN in a human that comprises the step of administering to said human a therapeutically effective amount of a MDM2 inhibitor, or a pharmaceutically acceptable salt thereof, wherein the MPN is selected from the group consisting of polycythemia vera (PV), essential thrombocythemia (ET), and primary myelofibrosis, wherein the therapeutically effective amount is 120 mg BID. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

A MDM2 inhibitor or a pharmaceutically acceptable salt thereof may also be used in combination with radiation therapy, hormone therapy, surgery and immunotherapy, which therapies are well known to those skilled in the art, for treating a MPN selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the myelofibrosis is selected from the group consisting of primary myelofibrosis (PMF), post-polycythemia vera myelofibrosis (post-PV MF), and post-essential thrombocythemia myelofibrosis (post-ET MF). In an embodiment, the primary myelofibrosis (PMF) is selected from the group consisting of prefibrotic/early stage PMF and overt fibrotic stage PMF. In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T).

Methods of Treating Chronic Myelogenous Leukemia (CML) and Acute Myelogenous Leukemia (AML)

The present invention relates to a method of treating chronic myelogenous leukemia (CML) comprising the step of administering to a human in need thereof a Mouse double minute 2 homolog (MDM2) inhibitor, or a pharmaceutically acceptable salt thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

The present invention relates to a use of a Mouse double minute 2 homolog (MDM2) inhibitor, or a pharmaceutically acceptable salt thereof, for treating chronic myelogenous leukemia (CML) in a human in need thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

The present invention relates to a method of treating acute myelogenous leukemia (AML) comprising the step of administering to a human in need thereof a Mouse double minute 2 homolog (MDM2) inhibitor, or a pharmaceutically acceptable salt thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

The present invention relates to a use of a Mouse double minute 2 homolog (MDM2) inhibitor, or a pharmaceutically acceptable salt thereof, for treating acute myelogenous leukemia (AML) in a human in need thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

Methods of Treating Chronic Merkel Cell Carcinoma

The present invention relates to a method of treating Merkel cell carcinoma (MCC) comprising the step of administering to a human in need thereof a Mouse double minute 2 homolog (MDM2) inhibitor, or a pharmaceutically acceptable salt thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

The present invention relates to a use of a Mouse double minute 2 homolog (MDM2) inhibitor, or a pharmaceutically acceptable salt thereof, for treating Merkel cell carcinoma (MCC) in a human in need thereof. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MDM2 inhibitor is administered to a human according to Section "Dosages and Dosing Regimens".

MDM2 Inhibitor

The compound of Formula (I) has the structure and name shown below.

2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl) acetic acid

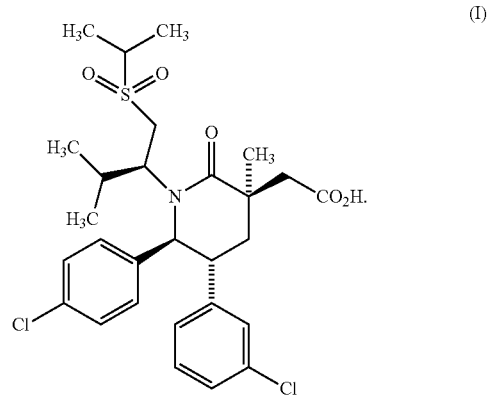

The synthesis of the compound of Formula (I) is set forth in International Applications: WO2011/153509 and WO2014/200937; U.S. Pat. Nos. 8,569,341; 9,593,129; 9,296,736; 9,623,018; 9,757,367; 9,801,867; 9,376,386; and 9,855,259, the disclosure of which are incorporated by reference herein in its entirety.

In an embodiment, the compound of Formula (I) or Formula (II) is in an amorphous form. In an embodiment, the MDM2 inhibitor is the compound of Formula (I) or Formula (II) in a crystalline form. In an embodiment, the MDM2 inhibitor is the compound of Formula (I) in a crystalline anhydrous form. In an embodiment, the MDM2 inhibitor is the compound of Formula (I) in a crystalline anhydrous form characterized by a powder X-ray diffraction pattern comprising peaks at diffraction angle 2 theta degrees at approximately 11.6, 12.4, 18.6, 19.0, 21.6 and 23.6. In an embodiment, the MDM2 inhibitor is the compound of Formula (I) in a crystalline anhydrous form having the X-ray diffraction pattern substantially shown in FIG. 1. The method of making such crystalline form was disclosed in the International Application WO2014200937, the disclosure of which is incorporated herein by reference in its entirety.

In an embodiment, the MDM2 inhibitor is a compound of Formula (II) having the structure and name shown below.

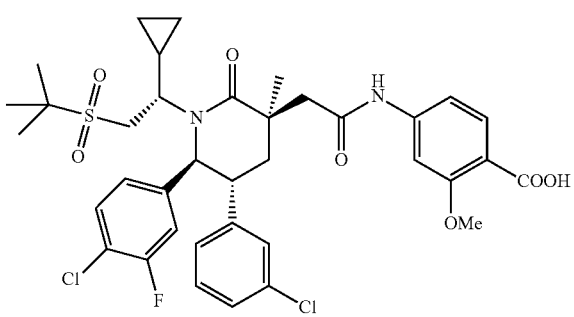

(II)

4-(2-((3R,5R,6S)-1-((S)-2-(tert-butyl sulfonyl)-1-cyclopropyl ethyl)-6-(4-chloro-3-fluorophenyl)-5-(3-chlorophenyl)-3-methyl-2-oxopiperidin-3-yl)acetamido)-2-methoxybenzoic acid The synthesis of the compound of Formula (II) is set forth in U.S. Pat. No. 8,952,036, the disclosure of which is incorporated by reference herein in its entirety.

RG7388 (Idasanutlin)

In an embodiment, the MDM2 inhibitor is RG7388. RG7388 has the chemical structure and name shown as:

4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid

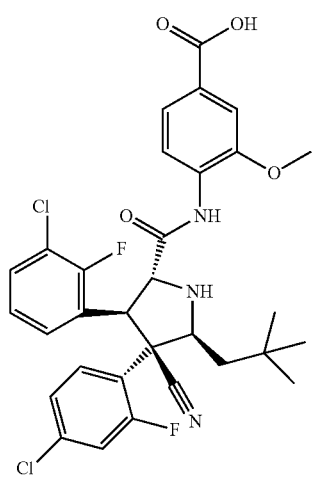

Triptolide (PG490)

In an embodiment, the MDM2 inhibitor is triptolide. Triptolide has the chemical structure and name shown as:

(5b S,6aS,7aS,8R,8aR,9aS,9b S, 10aS, 10bS)-8-hydroxy-8a-isopropyl-10b-methyl-2,5,5b,6,6a, 8,8a, 9a,9b, 10b-decahydrotris(oxireno) [2',3':4b,5;2'',3'': 6,7;2''',3''':8a,9] phenanthro[1,2-c]furan-3(1H)-one

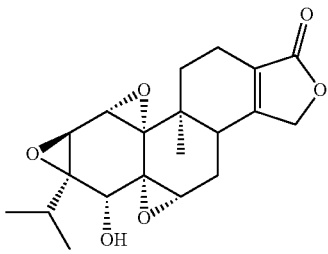

Nutlin-3a

In an embodiment, the MDM2 inhibitor is Nutlin-3a. Nutlin-3a has the chemical structure and name shown as:

4-[(4S,5R)-4,5-bis(4-chlorophenyl)-2-(4-methoxy-2-propan-2-yloxyphenyl)-4,5-dihydroimidazole-1-carbonyl]piperazin-2-one

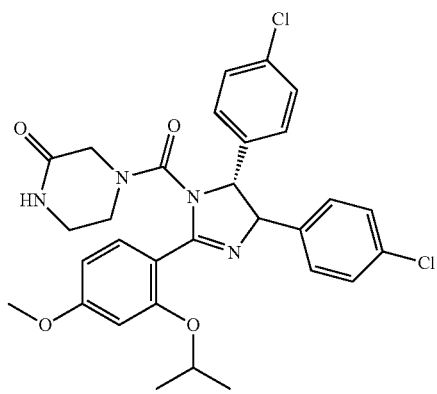 [SMILES: COc1ccc(C2=NC(c3ccc(Cl)cc3)[C@@H](c3ccc(Cl)cc3)N2C(=O)N2CCNC(=O)C2)c(OC(C)C)c1]

HDM201

In an embodiment, the MDM2 inhibitor is HDM201. HDM201 has the chemical structure and name shown as:

(4S)-5-(5-chloro-1-methyl-2-oxopyridin-3-yl)-4-(4-chlorophenyl)-2-(2,4-dimethoxypyrimidin-5-yl)-3-propan-2-yl-4H-pyrrolo[3,4-d]imidazol-6-one

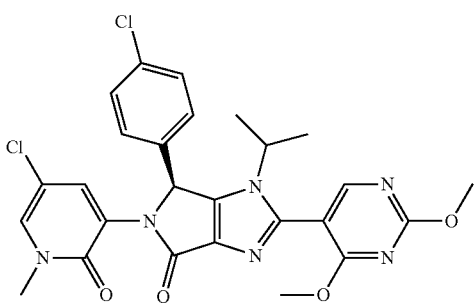 [SMILES: COc1ncc(-c2nc3c(n2C(C)C)[C@H](c2ccc(Cl)cc2)N(c2cc(Cl)cn(C)c2=O)C3=O)c(OC)n1]

RG7112

In an embodiment, the MDM2 inhibitor is RG7112. RG7112 has the chemical structure and name shown as:

[(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone

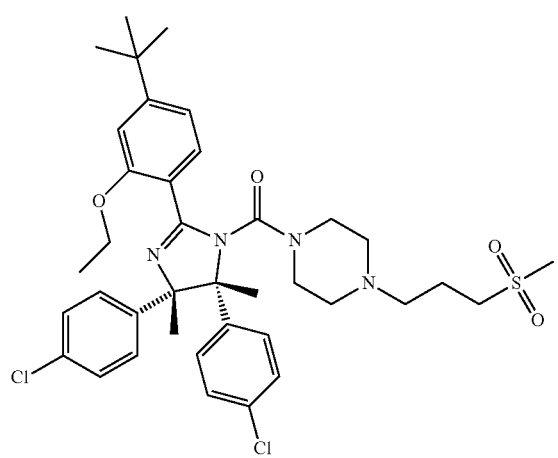 [SMILES: CCOc1cc(C(C)(C)C)ccc1C1=N[C@@](C)(c2ccc(Cl)cc2)[C@@](C)(c2ccc(Cl)cc2)N1C(=O)N1CCN(CCCS(C)(=O)=O)CC1]

CGM097A

In an embodiment, the MDM2 inhibitor is CGM097A. CGM097A has the chemical structure and name shown as:

(1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one

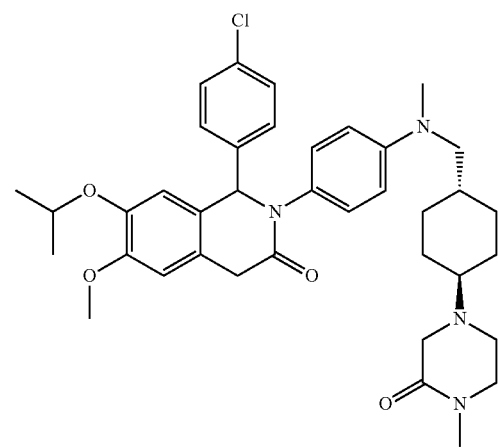 [SMILES: COc1cc2c(cc1OC(C)C)C(c1ccc(Cl)cc1)N(c1ccc(N(C)C[C@H]3CC[C@H](N4CCN(C)C(=O)C4)CC3)cc1)C(=O)C2]

Nutlin-3

In an embodiment, the MDM2 inhibitor is nutlin-3. Nutlin-3 has the chemical structure and name shown as:

4-[4,5-bis(4-chlorophenyl)-2-(4-methoxy-2-propan-2-yloxyphenyl)-4,5-dihydroimidazole-1-carbonyl]piperazin-2-one

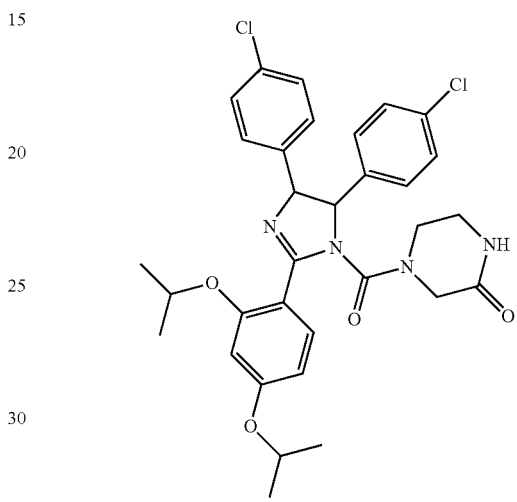

SJ-172550

In an embodiment, the MDM2 inhibitor is SJ-172550. SJ-172550 has the chemical structure and name shown as:

methyl 2-[2-chloro-6-ethoxy-4-[(3-methyl-5-oxo-1-phenylpyrazol-4-ylidene)methyl]phenoxy]acetate

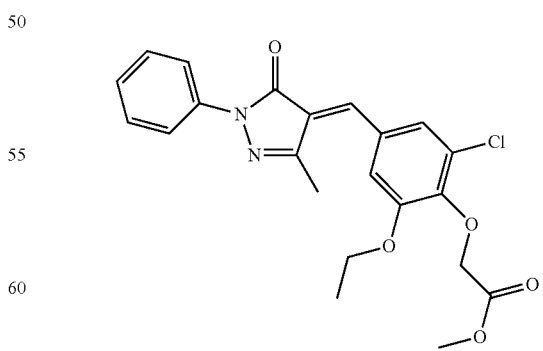

SAR405838 (MI-77301)

In an embodiment, the MDM2 inhibitor is SAR405838. SAR405838 has the chemical structure and name shown as:

41

(2'R,3R,3'S,5'S)-6-chloro-3'-(3-chloro-2-fluorophenyl)-5'-(2,2-dimethylpropyl)-N-(4-hydroxycyclohexyl)-2-oxospiro[1H-indole-3,4'-pyrrolidine]-2'-carboxamide

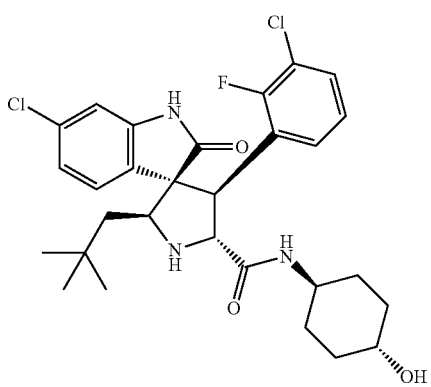 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]

MI-773

In an embodiment, the MDM2 inhibitor is MI-773. MI-773 has the chemical structure and name shown as:

(2'R,3 S,3'S,5'R)-6-chloro-3'-(3-chloro-2-fluorophenyl)-5'-(2,2-dimethylpropyl)-N-(4-hydroxycyclohexyl)-2-oxospiro[1H-indole-3,4'-pyrrolidine]-2'-carboxamide

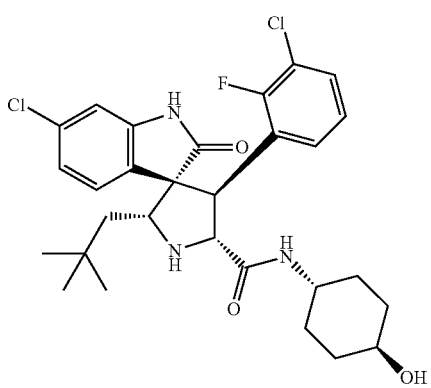 [SMILES: CC(C)(C)C[C@H]1N[C@@H](C(=O)N[C@H]2CC[C@H](O)CC2)[C@H](c2cccc(Cl)c2F)[C@@]12C(=O)Nc1cc(Cl)ccc12]

MX69

In an embodiment, the MDM2 inhibitor is MX69. MX69 has the chemical structure and name shown as:

42

4-[8-[(3,4-dimethylphenyl)sulfamoyl]-3a,4,5,9b-tetrahydro-3H-cyclopenta[c]quinolin-4-yl]benzoic acid

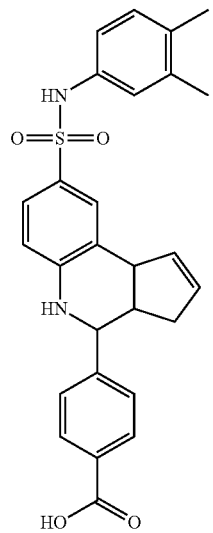 [SMILES: Cc1ccc(NS(=O)(=O)c2ccc3c(c2)C2C=CCC2C(c2ccc(C(=O)O)cc2)N3)cc1C]

Y11239-EE

In an embodiment, the MDM2 inhibitor is YH239-EE. YH239-EE has the chemical structure and name shown as:

ethyl 3-[2-(tert-butylamino)-1-[(4-chlorophenyl)methyl-formylamino]-2-oxoethyl]-6-chloro-1H-indole-2-carboxylate

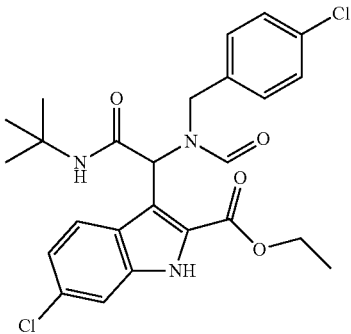 [SMILES: CCOC(=O)c1[nH]c2cc(Cl)ccc2c1C(C(=O)NC(C)(C)C)N(C=O)Cc1ccc(Cl)cc1]

RO8994

In an embodiment, the MDM2 inhibitor is RO8994. RO8994 has the chemical structure and name shown as:

(2'R,3R,3'S,5'S)—N-(4-carbamoyl-2-methoxyphenyl)-6-chloro-3'-(3-chloro-2-fluorophenyl)-5'-(2,2-dimethylpropyl)-2-oxospiro[1H-indole-3,4'-pyrrolidine]-2'-carboxamide

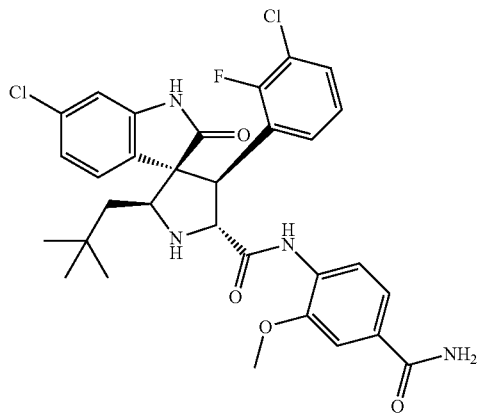 [SMILES: COc1cc(C(N)=O)ccc1NC(=O)[C@@H]1N[C@@H](CC(C)(C)C)[C@@]2(C(=O)Nc3cc(Cl)ccc32)[C@H]1c1cccc(Cl)c1F]

Nutlin-3b

In an embodiment, the MDM2 inhibitor is nutlin-3b. Nutlin-3b has the chemical structure and name shown as:

4-[(4R,5S)-4,5-bis(4-chlorophenyl)-2-(4-methoxy-2-propan-2-yloxyphenyl)-4,5-dihydroimidazole-1-carbonyl]piperazin-2-one

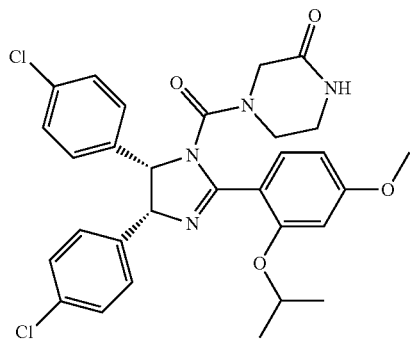 [SMILES: COc1ccc(C2=N[C@H](c3ccc(Cl)cc3)[C@H](c3ccc(Cl)cc3)N2C(=O)N2CCNC(=O)C2)c(OC(C)C)c1]

Serdemetan (JNJ-26854165)

In an embodiment, the MDM2 inhibitor is Serdemetan. Serdemetan has the chemical structure and name shown as:

1-N-[2-(1H-indol-3-yl)ethyl]-4-N-pyridin-4-ylbenzene-1,4-diamine

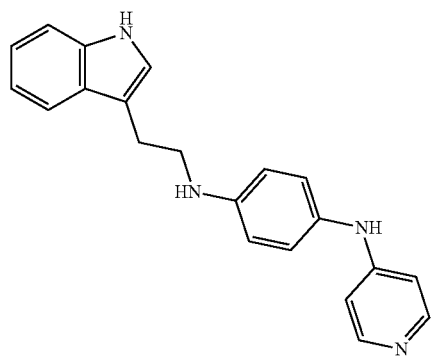 [SMILES: c1ccc2c(CCNc3ccc(Nc4ccncc4)cc3)c[nH]c2c1]

NSC59984

In an embodiment, the MDM2 inhibitor is NSC59984. NSC59984 has the chemical structure and name shown as:

(E)-1-(4-methylpiperazin-1-yl)-3-(5-nitrofuran-2-yl)prop-2-en-1-one

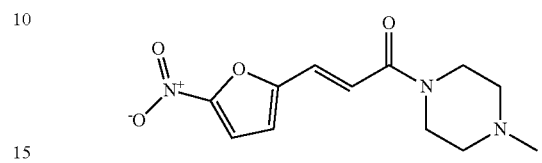

CHEMBL2386350

In an embodiment, the MDM2 inhibitor is CHEMBL2386350. CHEMBL2386350 has the chemical structure and name shown as:

2-[4-[(4S,5R)-2-(4-tert-butyl-2-ethoxyphenyl)-4,5-bis(4-chlorophenyl)-4,5-dimethylimidazole-1-carbonyl]piperazin-1-yl]-1-morpholin-4-ylethanone

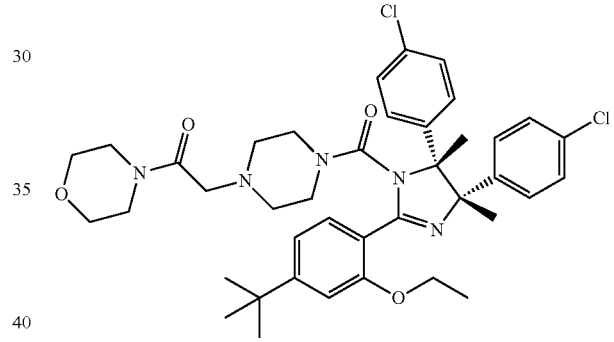

CGM0970B

In an embodiment, the MDM2 inhibitor is CGM0970B. CGM0970B has the chemical structure and name shown as:

(1R)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one

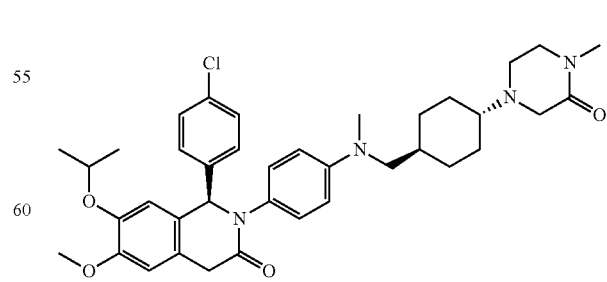

MK-8242

In an embodiment, the MDM2 inhibitor is MK-8242. MK-8242 has the chemical structure and name shown as:

4-amino-1-[(2R,3S,4S,5R)-3,4-dihydroxy-5-(hydroxymethyl)oxolan-2-yl]pyrimidin-2-one

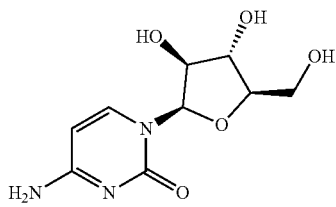 [SMILES: Nc1ccn([C@@H]2O[C@H](CO)[C@@H](O)[C@@H]2O)c(=O)n1]

DS-3032

In an embodiment, the MDM2 inhibitor is DS-3032. DS-3032 has the chemical structure and name shown as:

(3'R,4'S,5'R)—N-((3R,6S)-6-carbamoyltetrahydro-2H-pyran-3-yl)-6"-chloro-4'-(2-chloro-3-fluoropyridin-4-yl)-4,4-dimethyl-2"-oxodispiro[cyclohexane-1,2'-pyrrolidine-3',3"-indoline]-5'-carboxamide

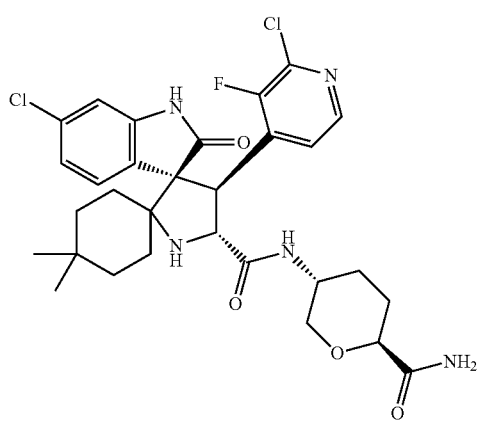 [SMILES: CC1(C)CCC2(CC1)N[C@@H](C(=O)N[C@@H]1CC[C@@H](C(N)=O)OC1)[C@H](c1ccnc(Cl)c1F)[C@]21C(=O)Nc2cc(Cl)ccc21]

DS-3032B

In an embodiment, the MDM2 inhibitor is DS-3032B. DS-3032B has the chemical structure and name shown as:

(3'R,4'S,5'R)—N-((3R,6S)-6-carbamoyltetrahydro-2H-pyran-3-yl)-6"-chloro-4'-(2-chloro-3-fluoropyridin-4-yl)-4,4-dimethyl-2"-oxodispiro[cyclohexane-1,2'-pyrrolidine-3',3"-indoline]-5'-carboxamide 4-methylbenzenesulfonate

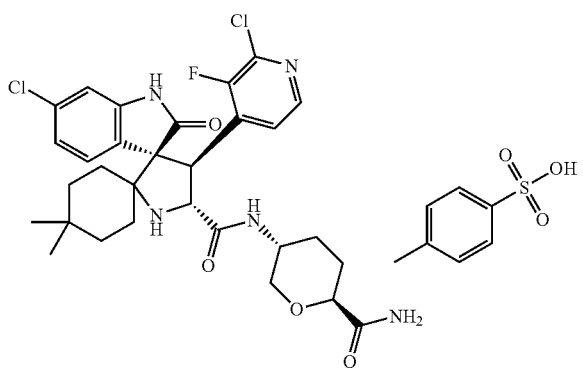

HDM201

In an embodiment, the MDM2 inhibitor is HDM201. HDM201 has the chemical structure and name shown as:

(4S)-5-(5-chloro-1-methyl-2-oxopyridin-3-yl)-4-(4-chlorophenyl)-2-(2,4-dimethoxypyrimidin-5-yl)-3-propan-2-yl-4H-pyrrolo[3,4-d]imidazol-6-one

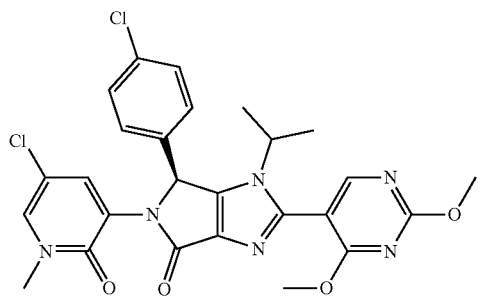

APG-115

In an embodiment, the MDM2 inhibitor is APG-115. APG-115 has the chemical structure and name shown as:

4-((3R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid

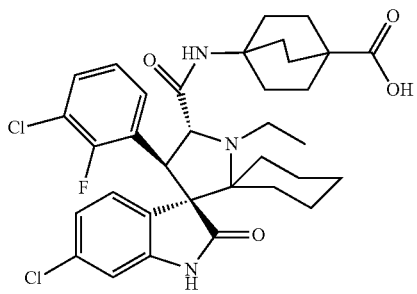 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

MI-1061

In an embodiment, the MDM2 inhibitor is APG-115. APG-115 has the chemical structure and name shown as:

4-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)benzoic acid

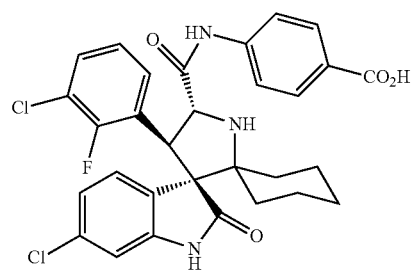 [SMILES: O=C(O)c1ccc(NC(=O)[C@@H]2NC3(CCCCC3)[C@@]3(C(=O)Nc4cc(Cl)ccc43)[C@H]2c2cccc(Cl)c2F)cc1]

Pharmaceutical Compositions

In some embodiments, the invention provides pharmaceutical compositions comprising a MDM2 inhibitor or a pharmaceutically acceptable salt thereof for treating cancer, wherein the cancer is selected from the group consisting of carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, head and neck, and skin (including basal and squamous cell carcinoma, melanoma skin cancer, Merkel cell carcinoma, Kaposi Sarcoma, skin lymphomas); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma, glioblastoma, and schwannomas); and other tumors (including melanoma, seminoma, teratocarcinoma, osteosarcoma, xenoderoma pigmentosum, keratoctanthoma, and thyroid follicular cancer). In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating a myeloproliferative neoplasm (MPN), wherein the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD), wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating chronic myelogenous leukemia (CML), wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating acute myelogenous leukemia (AML), wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating Merkel cell carcinoma (MCC), wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating a myeloproliferative neoplasm (MPN), wherein the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD), wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, the MDM2 inhibitor is a compound of Formula (I) or Formula (II). In some embodiments, the invention provides pharmaceutical compositions comprising the compound of Formula (I) or Formula (II) or a pharmaceutically acceptable salt thereof for treating a myeloproliferative neoplasm (MPN), wherein the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD).

In some embodiments, the invention provides pharmaceutical compositions comprising the compound of Formula (I) or Formula (II) or a pharmaceutically acceptable salt thereof for treating a myeloproliferative neoplasm (MPN), wherein the MPN is selected from the group consisting of polycythemia vera (PV), essential thrombocythemia (ET), and primary myelofibrosis.

In some embodiments, the invention provides pharmaceutical compositions comprising the compound of Formula (I) or Formula (II) or a pharmaceutically acceptable salt thereof for treating polycythemia vera (PV).

In some embodiments, the invention provides pharmaceutical compositions comprising a MDM2 inhibitor or a pharmaceutically acceptable salt thereof for treating polycythemia vera (PV), wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating polycythemia vera (PV), wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In some embodiments, the invention provides pharmaceutical compositions comprising the compound of Formula (I) or Formula (II) or a pharmaceutically acceptable salt thereof for treating essential thrombocythemia (ET).

In some embodiments, the invention provides pharmaceutical compositions comprising a MDM2 inhibitor or a pharmaceutically acceptable salt thereof for treating essential thrombocythemia (ET), wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating essential thrombocythemia (ET), wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In some embodiments, the invention provides pharmaceutical compositions comprising the compound of Formula (I) or Formula (II) or a pharmaceutically acceptable salt thereof or a pharmaceutically acceptable salt thereof for treating primary myelofibrosis.

In some embodiments, the invention provides pharmaceutical compositions comprising a MDM2 inhibitor or a pharmaceutically acceptable salt thereof for treating primary myelofibrosis, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In some embodiments, the invention provides pharmaceutical compositions comprising a MDM2 inhibitor or a pharmaceutically acceptable salt thereof for treating primary myelofibrosis, wherein the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, myelofibrosis is selected from primary myelofibrosis (PMF), post-polycythemia vera myelofibrosis (post-PV MF), and post-essential thrombocythemia myelofibrosis (post-ET MF).

The pharmaceutical compositions are typically formulated to provide a therapeutically effective amount of a MDM2 inhibitor or a pharmaceutically acceptable salt thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants. Where desired, other ingredients in addition to a MDM2 inhibitor or a pharmaceutically acceptable salt thereof may be mixed into a preparation or both components may be formulated into separate preparations for use in combination separately or at the same time.

In selected embodiments, the concentration of a MDM2 inhibitor or a pharmaceutically acceptable salt thereof provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v.

In selected embodiments, the concentration of a MDM2 inhibitor or a pharmaceutically acceptable salt thereof provided in the pharmaceutical compositions of the invention is independently greater than 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v.

In selected embodiments, the concentration of a MDM2 inhibitor or a pharmaceutically acceptable salt thereof is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2%, to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v.

In selected embodiments, the concentration of a MDM2 inhibitor or a pharmaceutically acceptable salt thereof is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In selected embodiments, the amount of a MDM2 inhibitor or a pharmaceutically acceptable salt thereof is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of a MDM2 inhibitor or a pharmaceutically acceptable salt thereof is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g or 10 g.

A MDM2 inhibitor or a pharmaceutically acceptable salt thereof are effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting exemplary pharmaceutical compositions and methods for preparing the same.

Pharmaceutical Compositions for Oral Administration

In selected embodiments, the invention provides a pharmaceutical composition for oral administration comprising a MDM2 inhibitor or a pharmaceutically acceptable salt thereof, and a pharmaceutical excipient suitable for oral administration.

In selected embodiments, the invention provides a solid pharmaceutical composition for oral administration containing: (i) an effective amount of a MDM2 inhibitor or a pharmaceutically acceptable salt thereof, in combination and (ii) a pharmaceutical excipient suitable for oral administration. In selected embodiments, the composition further contains (iii) an effective amount of at least one additional active ingredient.

In selected embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A MDM2 inhibitor or a pharmaceutically acceptable salt thereof can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use, such as for compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Examples may include, but are not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection comprising a MDM2 inhibitor or a pharmaceutically acceptable salt thereof, and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating a MDM2 inhibitor or a pharmaceutically acceptable salt thereof in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of a MDM2 inhibitor or a pharmaceutically acceptable salt thereof or pharmaceutical composition of these compounds can be effected by any method that enables delivery of the compounds to the site of action. These methods include oral routes, intraduodenal routes, parenteral injection (including intravenous, intra-arterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a MDM2 inhibitor or a pharmaceutically acceptable salt thereof, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer. In an embodiment, the invention provides a kit comprising a MDM2 inhibitor or a pharmaceutically acceptable salt thereof for use in the treatment of a MPN. In an embodiment, the MPN is selected from the group consisting of polycythemia vera (PV), essential thrombocythemia (ET), and primary myelofibrosis. In an embodiment, the invention provides a kit comprising a MDM2 inhibitor or a pharmaceutically acceptable salt thereof for use in the treatment of chronic myelogenous leukemia (CML). In an embodiment, the invention provides a kit comprising a MDM2 inhibitor or a pharmaceutically acceptable salt thereof for use in the treatment of acute myelogenous leukemia (AML). In an embodiment, the invention provides a kit comprising a MDM2 inhibitor or a pharmaceutically acceptable salt thereof for use in the treatment of Merkel cell carcinoma (MCC).

Dosages and Dosing Regimens

The amount of a MDM2 inhibitor or a pharmaceutically acceptable salt thereof administered will be dependent on the human being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In some embodiments, a MDM2 inhibitor or a pharmaceutically acceptable salt thereof is administered in a single dose. Typically, such administration will be by injection—e.g., intravenous injection, in order to introduce the agents quickly. However, other routes may be used as appropriate. A single dose of a MDM2 inhibitor or a pharmaceutically acceptable salt thereof may also be used for treatment of an acute condition.

In some embodiments, a MDM2 inhibitor or a pharmaceutically acceptable salt thereof is administered in multiple doses for treating a MPN. In an embodiment, a MDM2 inhibitor or a pharmaceutically acceptable salt thereof is administered in multiple doses. In an embodiment, a MDM2 inhibitor or a pharmaceutically acceptable salt thereof is administered in multiple doses by injection—e.g., intravenous injection. In an embodiment, dosing may be once, twice, three times, four times, five times, six times, or more than six times per day. In an embodiment, dosing may be selected from the group consisting of once a day, twice a day, three times a day, four times a day, five times a day, six times a day, once every other day, once weekly, twice weekly, three times weekly, four times weekly, biweekly, and monthly. In other embodiments, a MDM2 inhibitor or a pharmaceutically acceptable salt thereof is administered about once per day to about six times per day. In some embodiments a MDM2 inhibitor or a pharmaceutically acceptable salt thereof is administered once daily, while in other embodiments a MDM2 inhibitor or a pharmaceutically acceptable salt thereof is administered twice daily, and in other embodiments a MDM2 inhibitor or a pharmaceutically acceptable salt thereof is administered three times daily. In some embodiments a MDM2 inhibitor or a pharmaceutically acceptable salt thereof is administered three times a week, including every Monday, Wednesday, and Friday.

Administration of a MDM2 inhibitor or a pharmaceutically acceptable salt thereof may continue as long as necessary. In some embodiments, a MDM2 inhibitor or a pharmaceutically acceptable salt thereof is administered for more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. In some embodiments, a MDM2 inhibitor or a pharmaceutically acceptable salt thereof is administered for less than 28, 14, 7, 6, 5, 4, 3, 2, or 1 day. In some embodiments, a MDM2 inhibitor or a pharmaceutically acceptable salt thereof is administered for about 14 days, about 21 days, about 28 days, about 35 days, about 42 days, about 49 days, or about 56 days. In some embodiments, a MDM2 inhibitor or a pharmaceutically acceptable salt thereof is administered chronically on an ongoing basis—e.g., for the treatment of chronic effects. In another embodiment the administration of a MDM2 inhibitor or a pharmaceutically acceptable salt thereof continues for less than about 7 days. In yet another embodiment the administration continues for more than about 6, 10, 14, 28 days, two months, three months, four months, five months, six months, seven months, eight months, nine months, ten months, eleven months or one year. In some embodiments, the administration continues for more than about one year, two years, three years, four years, or five years. In some embodiments, continuous dosing is achieved and maintained as long as necessary.

In some embodiments, an effective dosage of a MDM2 inhibitor or a pharmaceutically acceptable salt thereof is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a MDM2 inhibitor or a pharmaceutically acceptable salt thereof is about 15 mg, about 25 mg, about 30 mg, about 50 mg, about 50 mg, about 75 mg, about 90 mg, about 100 mg, about 120 mg, about 125 mg, about 150 mg, about 175 mg, about 180 mg, about 200 mg, about 225 mg, about 240 mg, about 250 mg, about 275 mg, about 300 mg, about 325 mg, about 350 mg, about 360 mg, about 375 mg, about 400 mg, about 425 mg, about 450 mg, about 475 mg, about 480 mg, or about 500 mg. In some embodiments, an effective dosage of a MDM2 inhibitor or a pharmaceutically acceptable salt thereof is 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

In some embodiments, an effective dosage of a MDM2 inhibitor or a pharmaceutically acceptable salt thereof is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a MDM2 inhibitor or a pharmaceutically acceptable salt thereof is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a MDM2 inhibitor or a pharmaceutically acceptable salt thereof is administered at a dosage of 10 to 500 mg BID, including a dosage of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg BID.

In some embodiments, a MDM2 inhibitor or a pharmaceutically acceptable salt thereof is administered at a dosage of 10 to 500 mg QD, including a dosage of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg QD.

An effective amount of a MDM2 inhibitor or a pharmaceutically acceptable salt thereof may be administered in either single or multiple doses by any of the accepted modes of administration of agents having similar utilities, including buccal, sublingual, and transdermal routes, by intra-arterial injection, intravenously, parenterally, intramuscularly, subcutaneously or orally.

In some embodiments, a MDM2 inhibitor or a pharmaceutically acceptable salt thereof is administered to a subject intermittently, known as intermittent administration. By "intermittent administration", it is meant a period of administration of a therapeutically effective dose of a MDM2 inhibitor or a pharmaceutically acceptable salt thereof, followed by a time period of discontinuance, which is then followed by another administration period and so on. In each administration period, the dosing frequency can be independently select from three times daily, twice daily, daily, once weekly, twice weekly, three times weekly, four times weekly, five times weekly, six times weekly or monthly. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

By "period of discontinuance" or "discontinuance period" or "rest period", it is meant to the length of time when discontinuing of the administration of a MDM2 inhibitor or a pharmaceutically acceptable salt thereof. The time period of discontinuance may be longer or shorter than the administration period or the same as the administration period. During the discontinuance period, other therapeutic agents other than a MDM2 inhibitor or a pharmaceutically acceptable salt thereof may be administered.

In an embodiment, a MDM2 inhibitor or a pharmaceutically acceptable salt thereof is administered to a human subject in need thereof for treating a myeloproliferative neoplasm (MPN) for a first administration period, then followed by a discontinuance period, then followed by a second administration period, and so on, wherein the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating polycythemia vera (PV) for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof.

In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, a MDM2 inhibitor or a pharmaceutically acceptable salt thereof is administered to a human subject in need thereof for treating essential thrombocythemia (ET) for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating primary myelofibrosis for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating chronic myelogenous leukemia (CML) for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating acute myelogenous leukemia (AML) for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating Merkel cell carcinoma (MCC) for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a MDM2 inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject daily; and the discontinuance period is about two weeks. In an embodiment, the first administration period and the second administration period are about three weeks, in which a MDM2 inhibitor or a pharmaceutically acceptable salt thereof is administered to a subject weekly; and the discontinuance period is about two weeks. In an embodiment, the first administration period and the second administration period are about four weeks, in which a MDM2 inhibitor or a pharmaceutically acceptable salt thereof is administered to a subject daily; and the discontinuance period is about two weeks. In an embodiment, the first administration period and the second administration period are about four weeks, in which a MDM2 inhibitor or a pharmaceutically acceptable salt thereof is administered to a subject weekly; and the discontinuance period is about two weeks. In an embodiment, the MDM2 inhibitor is the compound of Formula (I) or Formula (II). In an embodiment, the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating cancer on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof, wherein the cancer is selected from the group consisting of carcinomas such as cancer of the bladder, breast, colon, rectum, kidney, liver, lung (small cell lung cancer, and non-small-cell lung cancer), esophagus, gallbladder, ovary, pancreas, stomach, cervix, thyroid, prostate, head and neck, and skin (including basal and squamous cell carcinoma, melanoma skin cancer, Merkel cell carcinoma, Kaposi Sarcoma, skin lymphomas); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma, glioblastoma, and schwannomas); and other tumors (including melanoma, seminoma, teratocarcinoma, osteosarcoma, xenoderoma pigmentosum, keratoctanthoma, and thyroid follicular cancer). In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating a MPN on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof, wherein the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating primary myelofibrosis on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating polycythemia vera on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating phlebotomy-dependent polycythemia vera on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD). In an embodiment, the human subject is hydroxyurea (HU) intolerant (unacceptable side effects). In an embodiment, the human subject is hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed Ruxolitinib therapy.

In an embodiment, a MDM2 inhibitor or a pharmaceutically acceptable salt thereof is administered to a subject in need thereof for treating essential thrombocythemia on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating chronic myelogenous leukemia (CML) on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating acute myelogenous leukemia (AML) on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a subject in need thereof for treating Merkel cell carcinoma (MCC) on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof.

In an embodiment, a MDM2 inhibitor or a pharmaceutically acceptable salt thereof is administered to a human subject in need thereof for treating cancer on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-032, DS-3032B, APG-115, MI-1601, and pharmaceutically acceptable salts thereof, wherein the cancer is selected from the group consisting of carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, head and neck, and skin (including basal and squamous cell carcinoma, melanoma skin cancer, Merkel cell carcinoma, Kaposi Sarcoma, skin lymphomas); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma, glioblastoma, and schwannomas); and other tumors (including melanoma, seminoma, teratocarcinoma, osteosarcoma, xenoderma pigmentosum, keratoctanthoma, and thyroid follicular cancer). In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating a MPN on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof, wherein the MPN is selected from the group consisting of polycythemia vera (PV), myelofibrosis, primary myelofibrosis, thrombocythemia, essential thrombocythemia (ET), idiopathic myelofibrosis, systemic mastocystosis (SM), chronic neutrophilic leukemia (CNL), myelodysplastic syndrome (MDS), and systemic mast cell disease (SMCD). In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating primary myelofibrosis on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human in need thereof for treating polycythemia vera on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating essential thrombocythemia on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating chronic myelogenous leukemia (CML) on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating acute myelogenous leukemia (AML) on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating Merkel cell carcinoma (MCC) on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a MDM2 inhibitor or a pharmaceutically acceptable salt thereof is administered to a human subject in need thereof for treating phlebotomy-dependent polycythemia vera on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks, wherein the MDM2 inhibitor is selected from the group consisting of a compound of Formula (I), Formula (II), RG7388, Triptolide, HDM201, RG7112, CGM097A, CGM0970B, SJ-172550, SAR405838, MI-773, MX69, YH239-EE, RO8994, Nutlin-3, Nutlin-3a, Nutlin-3b, Serdemetan, NSC59984, CHEMBL2386350, MK-8242, DS-3032, DS-3032B, APG-115, MI-1601, and pharmaceutically acceptable salts thereof. In an embodiment, the MDM2 inhibitor is selected from the group consisting of a compound of Formula (I), Formula (II), RG7388, HDM201, RG7112, CGM097A, CGM0970B, SAR405838, MK-8242, DS-3032B, APG-115, MI-1601, and pharmaceutically acceptable salts thereof. In an embodiment, the MDM2 inhibitor is a compound of Formula (I) or Formula (II) and a pharmaceutically acceptable salt thereof; and the MDM 2 inhibitor is orally administered at a dose of 120 mg or 240 mg once a day (QD).

In an embodiment, a compound of Formula (I) or Formula (II) or a pharmaceutically acceptable salt thereof is administered to a human subject daily at a dose of 120 mg in need thereof for treating phlebotomy-dependent polycythemia vera on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks. In an embodiment, the human subject is hydroxyurea (HU) intolerant (unacceptable side effects). In an embodiment, the human subject is hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed Ruxolitinib therapy.

In an embodiment, a compound of Formula (I) or Formula (II) or a pharmaceutically acceptable salt thereof is administered to a human subject daily at a dose of 240 mg in need thereof for treating phlebotomy-dependent polycythemia vera on days 1-7 of a 28-day cycle (on days 8-28, the MDM2 inhibitor is not administered) for a period selected from 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, 104 weeks, 108 weeks, 112 weeks, 116 weeks, 120 weeks, 124 weeks, 128 weeks, 132 weeks, 136 weeks, 140 weeks, 144 weeks, 148 weeks, 152 weeks, and 156 weeks. In an embodiment, the human subject is determined as hydroxyurea (HU) intolerance (unacceptable side effects). In an embodiment, the human subject is hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed Ruxolitinib therapy.

In an embodiment, a compound of Formula (I) or Formula (II) or a pharmaceutically acceptable salt thereof is administered to a human subject daily at a dose of 120 mg in need thereof for treating phlebotomy-dependent polycythemia vera on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks. In an embodiment, the human subject is hydroxyurea (HU) intolerant (unacceptable side effects). In an embodiment, the human subject is hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed Ruxolitinib therapy.

In an embodiment, a compound of Formula (I) or Formula (II) or a pharmaceutically acceptable salt thereof is administered to a human subject daily at a dose of 240 mg in need thereof for treating phlebotomy-dependent polycythemia vera on days 1-7 of a 21-day cycle (on days 8-21, the MDM2 inhibitor is not administered) for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks. In an embodiment, the human subject is hydroxyurea (HU) intolerant (unacceptable side effects). In an embodiment, the human subject is hydroxyurea (HU) resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed Ruxolitinib therapy.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1

Effects of the Compound of Formula (I) on Polycythemia Vera Cells

The procedure of testing the effects of the compound of Formula (I) on polycythemia vera cells follows that described in Lu et al., Blood, 2012, 120(15); 3098-3105, the entirety of which is incorporated by reference. The following describes the procedure briefly.

Cell Preparation:

Peripheral blood will be obtained from polycythemia vera (PV) patients. Appropriate approval will be obtained from the Institutional Review Board. Informed consent will be obtained before the study. All patients will meet the World Health Organization diagnostic criteria for polycythemia vera (PV). The peripheral blood samples are layered onto Ficoll-Hypaque (1.077 g/mL; GE Healthcare) and low-density mononuclear cells are separated via centrifugation. The CD34+ cells will be isolated using a human CD34+ cell selection kit (StemCell Technologies) according to the manufacturer's instructions. The purity of the CD34+ cell population will be analyzed using a FACSCalibur flow cytometer (BD Biosciences); and is required for at least 85% for all experiments. Fresh normal human bone marrow CD34+ cells will be purchased from ALLCELLS as a control.

HPC Assays

The effects of the compound of Formula (I) on polycythemia vera (PV) patients can be assessed by the HPC assays, described in Lu et al., Blood, 2012, 3098-3105, the entirety of which is incorporated by reference. In brief, CD34+ cells will be cultured in serum free medium (StemCell Technologies) containing 50 ng/mL stem cell factor (SCF), 50 ng/mL thrombopoietin (TPO), 50 ng/mL fms-like tyrosine kinase 3 (Flt-3) ligand, and 50 ng/mL IL-3, and will be treated with various dose of the compound of Formula (I) for 4 days. After 4 days of treatment, CD34+ cells will be assayed in semisolid media as described in Bruno et al., Blood, 2006, 3128-3134, the entirety of which is incorporated by reference. Briefly, $5\times10^2$ CD34+ cells will be plated per dish in duplicate cultures containing 1 mL IMDM with 1.1% methylcellulose and 20% FBS, to which SCF, TPO, Flt-3 ligand, IL-3, and GM-CSF at each 50 ng/mL, and 2 U/mL erythropoietin (EPO) will be added. Colonies will be enumerated after 14 days of incubation, and individual colonies will be plucked and genotyped for JAK2V617F.

Nested Allele-Specific PCR for JAK2V617F-Positive Colonies

Genomic DNA will be isolated from randomized plucked colonies using the Extract-N-Amp Blood PCR Kits (Sigma-Aldrich). JAK2V617F will be detected by using a nested allele-specific PCR as described in Bruno et al., Blood, 2006, 3128-3134, the entirety of which is incorporated by reference. The final PCR products will be analyzed on 2.0% agarose gels. A 279-bp product indicates allele-specific JAK2V617F-positive, whereas a 229-bp product indicates JAK2V617F-negative. Colonies will be classified as homozygous for JAK2V617F if they contained only the 279-bp band, whereas heterozygous colonies will be identified based on the presence of both the 279-bp and 229-bp bands.

Apoptosis Assay

Treated cells will be collected and washed with PBS for staining with annexin-V (BD Biosciences); the staining procedures will be performed according to the protocols provided by the manufacturer. Data will be acquired on a FACSCalibur flow cytometer (BD Biosciences), and at least 10 000 live cells will be acquired for each analysis (BD FACS Diva software; BD Biosciences).

Western Blot Analysis

CD34+ cells will be purified from the peripheral blood of patients with polycythemia vera (PV) and cultured in serum-free medium contained with SCF, FL-3 ligand, IL-3, and TPO. The cells will be treated with various dose of the compound of Formula (I) for 4 hours. Cells will be harvested and the whole cells protein extracts will be prepared with RIPA lysis buffer (Boston BioProducts) for Western blotting.

To prepare the cytoplasmic and nuclear protein fractions of cells from patients with polycythemia vera (PV), CD34+ cells will be expanded in serum-free media containing SCF, FL-3 ligand, and IL-3 for 10 days. CD34+ cells will be then repurified and treated with various doses of the compound of Formula (I) for 48 hours in the presence of SCF, FL-3 ligand, IL-3, and TPO. The protein extracts will be prepared using the NE-PER nuclear and cytoplasmic extraction reagent (Thermo Scientific) according to the manufacturer's instructions.

Before Western blotting, all the samples will be denatured with Laemmli SDS-sample buffer (Boston BioProducts) by heating at 95° C. for 5 minutes; each sample will be separated on SDS-PAGE gels and transferred to polyvinylidifluoridine membranes (Bio-Rad). Phospho-p53, p53, MDM2, p21, p-STAT1, PUMA, and Bak were visualized using the antibodies (Cell Signaling Technologies) and ECL Western blotting reagents (Denville Scientific).

Statistical Analysis

Results will be reported as the mean±SD of individual data points obtained from the various number of experiments. Statistical significance will be determined using Student t tests or paired-samples t test.

Example 2

Effects of the Compound of Formula (I) on Essential Thrombocythemia Cells

The experiments will be run according to Example 1, except essential thrombocythemia Cells will be used in the place of polycythemia vera (PV) cells.

Example 3

Effects of the Compound of Formula (I) on Primary Myelofibrosis Cells

The experiments will be run according to Example 1, except primary myelofibrosis cells will be used in the place of polycythemia vera (PV) cells.

Example 4

The Compound of Formula (I) as a Monotherapy for Patients with Polycythemia Vera The purpose of this study is to investigate the safety and efficacy of the compound of Formula (I) with polycythemia vera (PV) patients. Similar clinical study with RG7388 is undergoing (NCT02407080). 30 polycythemia vera (PV) patients will be enrolled in the study and will be administered the compound of Formula (I) at 120 mg once daily (QD) on days 1-7 on a 21-days cycle (on days 8-21, no administration of the compound of Formula (I)) for two years. The inclusion criteria are as follows:
  JAK2V617F-positive polycythemia vera (PV)
  Previously non-treated with at least one other agent (hydroxyurea, interferon, anagrelide)
  ≥18 years of age
  Acceptable pre-study organ function during screening as defined as: Total bilirubin ≤1.5 times the upper limit of normal (ULN) unless due to Gilbert's disease or hemolysis, Aspartate aminotransferase (AST) and alanine aminotransferase (ALT)≤2.5 times ULN, Serum creatinine ≤1.5×ULN
  Women of childbearing age and males must agree to use adequate contraception (i.e., hormonal or barrier method of birth control; abstinence) prior to study entry and for the duration of study participation. Should a female subject become pregnant or suspect she is pregnant while participating in this study, she should be excluded from the study immediately During or at the end of the study, each polycythemia vera (PV) patient will be evaluated by the following items to determine the safety and efficacy of the compound of Formula (I): 1) hematologic response; 2) JAK2V617F allele burden reduction; 3) changes in bone marrow histopathologic abnormalities; 4) reduction in baseline reticulin/collagen fibrosis; 5) incidence of venous and arterial thrombosis; and 5) changes in MPN related symptoms as measured by the MPN-SAF.

Example 5

The Compound of Formula (I) as a Monotherapy for Patients with Essential Thrombocythemia The investigational study will be run according to the procedures described in Example 4, except enrolling essential thrombocythemia (ET) patients instead of polycythemia vera (PV) patients.

Example 6

The Compound of Formula (I) as a Monotherapy for Patients with Primary Myelofibrosis The investigational study will be run according to the procedures described in Example 4, except enrolling primary myelofibrosis patients instead of polycythemia vera (PV) patients.

Example 7

The Efficacy of the Compound of Formula (I) Against Cancer

The procedure of testing the efficacy of the compound of Formula (I) against cancer was described in Canon et al., Molecular Cancer Therapeutics, 2015; 649-658 and Rew, et al., J. Med. Chem. 2012; 55; 4936-54, the entirety of which are incorporated by reference. The following describes the procedure briefly.

Cells

SJSA-1, HCT116, ACHN, NCI-H460, MOLM-13, RKO, MCF7, 22RV1, HT-29, PC-3, NCI-H82, NCI-SNU1, and MG-63 cells were purchased from the ATCC, and have since been authenticated by short tandem repeat analysis (PowerPlex 18D Kit from Promega). NCI-H2452, SW982, C32, SK-HEP-1, A375, RT4, RPMI-2650, MDA-MB-134-VI, NCI-H2347, and A427 cells were purchased from ATCC and used within 6 months. IGR-1 and CML-T1 cells were purchased from German Collection of Microorganisms and Cell Cultures (DSMZ) and used within 6 months. A375sq2 cells were generated by in vivo passaging A375 cells in mice. HCT116 $p53^{-/-}$ cells were obtained from Bert Vogelstein. KS-1 and SNG-M were purchased from the Japanese Collection of Research Bioresources (HSRRB) and used within 6 months. G-401, G-361, LS174T cells (purchased from ATCC), EOL-1 cells (purchased from DSMZ) and KP-4 cells (purchased from HSRRB) were used after 6 months of purchase.

Surface Plasmon Resonance (SRP) Spectroscopy Binding Assay

Materials: Biacore T100 instrument (GE Healthcare), CM5 sensor chip (BR-1000-12), amine couple kit (BR-1000-50) including 1-ethyl-3-(3-dimethylamine-propyl)carbodiimide hydrochloride (EDC), N-hydroxysuccinimide (NETS) and ethanolamine-HCl, GST capture kit (BR-1002-23), HBS-N buffer (BR-1006-70) were from GE Healthcare. All buffers were filtered through 0.2 μM nylon membrane (VWR 87006-076). Kinetics study of inhibitors on Biacore: CM5 chip was preconditioned with 10 mM NaOH, 10 mM HCl and 0.1% SDS each for 10 s injection twice at 100 μL/min in HBS-N buffer. Immobilization and capture steps were performed as described: 1. Equal volume of 0.4 M EDC and 0.1 M NHS was mixed and injected over the chip surface to activate it for 10 min at 10 μL/min; 2. Anti-GST antibody (30 μg/ml in 10 mM sodium acetate, pH5) was immobilized to the chip by being injected to the surface for 15 min at 8 μ/min; 3. To deactivate excess reactive groups and wash off unbound anti-GST antibody, 1 M ethanolamine-HCl pH 8.5 was pumped across the surface for 10 min at 8 μL/min. The resulting antibody immobilization level was about 18000 RU; 4. 10 μg/ml GST in HBS-N buffer was injected over one flow cell for 15 min at 5 μl/min to create control surface of 1500 RU; 5. Sample surface was generated by injecting 20 μg/ml MDM2 over another flow cell for 15 min twice at 5 μ/min to reach capture level about 2000 RU. The kinetic binding study of inhibitors (molecular weight ranging from 450-600) was performed at 25° C. at a constant flow of 90 μL/min. The sample analysis buffer consisted of 25 mM Tris, pH 7.5, 150 mM NaCl, 0.005% (v/v) Tween 20, 0.2 mM TCEP plus 2.5% (v/v) DMSO. The inhibitors were diluted from 1 mM stock (in 100% DMSO) in sample analysis buffer to 12 nM. The inhibitors were then serially diluted 2 times to generate 8 points. Diluted inhibitors were injected over the control and sample surface for 1-2 minutes and dissociation observed for 3-4 minutes. Buffer containing 2.3-3.5% DMSO were injected to construct a DMSO correction curve. All the sensorgrams were processed using Biacore Evaluation software (GE Healthcare) with double reference procedure and DMSO calibration. KD values were established using a 1:1 binding model including a mass transfer limitation term.

SJSA-1 Cell Proliferation Assay (Click-iT EdU HCS Assay)

SJSA-1 cells were plated at a density of $2.89 \times 10^3$ cells/well in 384-well cell culture plates (Perkin Elmer, #6007460) in 40 μl of growth medium (RPMI 1640 supplemented with 10 mM HEPES, 1 mM sodium pyruvate, 1× Penicillin-Streptomycin, 2 mM Glutamine, and 10% fetal bovine serum). The cells were cultured for 24 hours at 37° C. and 5% $CO_2$. The next day, cells were treated with MDM2 inhibitors for 16 hours in the presence of 10% human serum. On day 3, Click-iT EdU assay procedures were performed according to the manufacturer's instructions with assay volumes reduced to 25 μL to adjust for 384 well formats (Invitrogen, #C10357). In short, EdU (5-ethynyl-2'-deoxyuridine) was added to cells to a final concentration of 10 μM and incubated for 1 hour. After labeling, cells were fixed with 4% formaldehyde and permeabilized with 0.1% Triton-X 100. After washing, cells were incubated with Click-iT reaction buffer and then with nuclear stain. Cells were then washed and imaged using Opera High Content Screening System (Perkin Elmer). Percentage of EdU incorporation was calculated and used for IC50 calculations. IC50 values were determined using a four-parameter logistical (4PL) Hill model.

BrdU Proliferation Assay (HCT116 Specificity Assay)

The potency of MDM2 inhibitors was also determined by assaying the effect on cell proliferation by quantifying the amount of 5-bromo-2-deoxyuridine (BrdU) incorporation in compound-treated cells vs. DMSO-treated control cells. HCT116 p53WT or $p53^{-/-}$ cells were plated at a density of $6 \times 10^3$ cells/well in 96-well cell culture plates in 100 μl of growth medium (McCoy's 5A, 1× PSQ, and 10% fetal bovine serum (all components from Invitrogen)). The cells were initially cultured for 24 hours at 37° C. and 5% $CO_2$ before addition of compound. The MDM2 inhibitors were serially diluted in DMSO (Sigma #D2650), then diluted again in assay medium (McCoy's 5A, 1× PSQ, 10% human serum (Bioreclamation #HMSRM)) with a final DMSO concentration of 1%. The cells were incubated in the presence of inhibitor at 37° C. and 5% $CO_2$ for 16 hours and then pulsed with diluted BrdU labeling reagent (1:100 final dilution, Invitrogen #00-0103) for 1 hour at 37° C. and 5% $CO_2$. Following the BrdU pulse, the medium was removed and the cells were fixed and stained for BrdU incorporation. The amount of BrdU incorporation was assayed using either flow cytometry or the Cellomics Array Scan Vti plate reader with the Target Activation bioapplication. The percentage of BrdU-positive cells in the DMSO-treated control wells was used to normalize the signal and calculate percent inhibition for each of the compound-treated wells. Dose response curves were generated using XLFit software to calculate IC50 values for each inhibitor tested.

HCT116 p21 TaqMan® Assay (HCT116 Specificity Assay)

This assay was performed exactly as described above for the SJSA-1 p21 assay, with the following exceptions: growth medium for both HCT116 p53WT or p53$^{-/-}$ cells was composed of McCoy's 5A, 1× PSQ, and 10% fetal bovine serum (all components from Invitrogen).

Biochemical (HTRF) Assay

Materials: Human MDM2 (GST-thrombin-hMDM2(1-188)) was produced in house. It was expressed in *E coli* and purified by Glutathione Sepharose 4B, Q-HP and Superdex 200 column. Human p53 (Avi-TrxA-6His-Thrombin-S-tag-EK-p53(1-83)) was expressed in *E. coli* and passed though Ni-NTA, Hydroxyapatite, Superdex 75 columns to reach purity over 80%. Human serum was from Bioreclamation (HMSRM, non-filtered). Monoclonal anti GST antibody labeled with europium cryptate (Eu-anti-GST, 61GSTLB) and SA-Xlent (611SAXLB) were from Cisbio. DTT, BSA, $KH_2PO_4$, $Na_2HPO_4$, DMSO, NaCl and KF were all from Sigma. The serum-free reaction buffer is composed of 1.06 mM $KH_2PO_4$, 2.96 mM $Na_2HPO_4$, 0.155 M NaCl, 0.1% BSA and 1 mM DTT. HTRF assay in serum used reaction buffer added with 15% human serum. The assay plate for HTRF was White 384 Opti plates from Perkin Elmer (6007299). The Envison (Perkin Elmer) was set at excitation 320 nm. Emissions were measured at 665 and 615 nm and the ratio of Em665/Em615 represented the interaction of MDM2-p53. Time-resolved fluorescence was measured 50 flashes for both detectors with 60 μs delay after each excitation. The reading time was 300 μs. Vprep was a product from Velocity11. Wellmate microplate dispenser was from Thermo Scientific. Serial Killer was made in house. Methods (Determination of inhibitor potency in HTRF assay): 20 μL 1.5 mM inhibitor was serial diluted to 20 μL DMSO for 22 points by Serial Killer. 1 μL of such diluted inhibitor was transferred to reaction plate with 9 μL reaction buffer by Vprep. 10 μL 1 nM of MDM2 was dispensed to reaction plate and incubated with inhibitor for 20 minutes before 20 μL 1.25 nM of p53 was added. After 60 minutes, the detection mixture (10 μL, 1 nM SA-Xlent, 3 nM Eu-anti-GST and 0.5 M KF) was dispensed to the reaction mixture and the plate was read on Envision after 18 hrs incubation. Total reaction volume is 50 μL. MDM2, p53 and detection were delivered to assay plates by Wellmate. IC50 was determined from duplicate data. For HTRF assay in 15% serum: the sequence of addition was the same as serum-free assay. 10 μL of 12.5 nM MDM2 diluted in reaction buffer containing 30% human serum was added to 10 μL of buffer and compound mixture to generate serum at 15%. 20 nM p53 was diluted in buffer with 15% human serum. The detection buffer was in 15% serum with 10 nM SA-Xlent, 3 nM Eu-anti-GST and 0.5 M KF.

Immunoblot Analysis

Tumor cells were treated with DMSO (0.1%) or the compound of Formula (I) (0.1, 1, or 10 mmol/L). After 24 hours, protein lysates were collected, electrophoresed, and transferred to polyvinylidene difluoride membranes (Life Technologies). Primary antibodies: p53 (DO-1; Calbiochem), MDM2 (BD Pharmingen), p21 (R&D Systems), PUMA (Abeam), or β-actin-HRP (Sigma).

Cell Viability Assay (72 hours)

Cell lines were plated in 96- or 384-well plates at optimum initial seeding densities to ensure that cells did not reach confluency by the end of the assay. The cells were treated with DMSO control or the compound of Formula (I) at various concentrations for 72 hours. CellTiter-Glo Luminescent Cell Viability (Promega) or ATPlite 1 step Luminescent (PerkinElmer) assay kits were used to determine the numbers of viable cells. Luminescence was measured with an EnVision Multilabel Reader (PerkinElmer) for each cell line at time zero (V0) before the addition of compounds, as well as after 72 hours of compound treatment. Growth inhibition (GI) was calculated on a 200-point scale according to the following equations, where V72 was luminescence of DMSO control at 72 hours and T72 was luminescence of the compound-treated sample: if T72>V0, then GI=100×(1−((T72−V0)/(V72−V0))); if T72<V0, then GI=100×(1−((T72−V0)/V0)). GI values of 0, 100, and 200 represented uninhibited cell growth (i.e., DMSO control), cell stasis, and complete cell killing, respectively. Dose-response curves were generated using XLFit software (IDBS) to calculate IC50 values for the compound of Formula (I) in each cell line tested.

Animal Studies

All animal experimental procedures were conducted in accordance with Association for Assessment and Accreditation of Laboratory Animal Care standards. All studies utilized 4- to 6-week-old female athymic nude mice (Harlan Laboratories, Hsd: Athymic Nude-Foxn1nu). The mice were housed five per filter-capped cage in sterile housing in an environmentally controlled room (temperature 23±2° C., relative humidity 50±20%) on a 12-hour light/dark cycle. The mice were fed commercial rodent chow (Harlan Laboratories, #2920X) and received filter-purified tap water ad libitum. The mice were individually identified by microchips (Bio Medic Data Systems) that were implanted subcutaneously at least 2 days before the study.

Pharmacodynamic Assays

Tumor cells (SJSA-1: $5×10^6$ cells, HCT 116: $2×10^6$ cells) were injected subcutaneously into the flank of female athymic nude mice in a 2:1 ratio of cells to Matrigel (BD Bioscience). The compound of Formula (I) was administered by oral gavage when average tumor size reached approximately 300 to 450 mm$^3$ (n=4/group). Tumors were harvested after 1, 2, 4, 8, and 24 hours after dose (SJSA-1) or 6 hours after dose (HCT116) and snap-frozen in liquid nitrogen. Total RNA was purified using Qiagen RNeasy 96 kit (Qiagen). The levels of p21 and the housekeeping gene GAPDH were assayed from total RNA from each sample in technical duplicates by qRTPCR. The qRT-PCR reactions were assayed on the Applied Biosystems Prism 7900HT instrument and the data were analyzed with Applied Biosystems SDS2.2 software. The SDS2.2 software calculated the p21 and GAPDH copy number in each of the tumor samples. The copy number of p21 was normalized to the copy number of the GAPDH, and the fold increase of normalized p21 levels were calculated relative to vehicle control for each sample. For MIC-1, plasma was collected at the time of sacrifice and MIC-1 was detected using R&D Quantikine Human MIC-1 Immunoassay (cat no. DGD150) following the manufacturer's instructions. The ELISA assay was read using a Spectramax M5 microplate reader using Softmax pro v4 (Molecular Devices).

Xenograft Studies

SJSA-1 cells (5×106 cells with Matrigel at a ratio of 2:1), NCI-H460 cells (5×106 cells with Matrigel at a ratio of 2:1), A375sq2 (5×106 cells with Matrigel at a ratio of 2:1), or HCT116 (2 106 cells) were injected subcutaneously in the flank of female athymic nude mice (n=10/group). Treatment began when tumors were established and approximately 200 mm3. The compound of Formula (I) was administered once per day by oral gavage. Tumor dimensions were assessed twice weekly with a Pro-Max electronic digital caliper (Sylvac) and tumor volume was calculated using the formula: length×width×height and expressed as mm3. Data are expressed as mean±SEM. Body weight was recorded twice weekly to assess tolerability (data not shown). Analysis of p21 mRNA at the end of the xenograft studies was performed as described for the p21 pharmacodynamic assay.
Detection of BrdUrd and Cleaved Caspase-3 in Xenografts Tumors were harvested 6 hours after the last treatment, formalin fixed, and processed into paraffin. Two hours before harvest, mice were intraperitoneally injected with BrdUrd (50 mg/kg). Tumor sections were immunostained for either BrdUrd or cleaved capsase-3 using commercial antibodies and counterstained with hematoxylin. Sections were scanned at ×20 via the Aperio Digital Scanner and positive nuclear densities were determined using Visiomorph image analysis software.

Statistical Analysis

For in vivo the compound of Formula (I) dose-response efficacy studies, repeated measures ANOVA (RMANOVA) followed by the Dunnett post hoc test for multiple comparisons was used to evaluate statistical significance of observed differences.

Results

Figure 2:
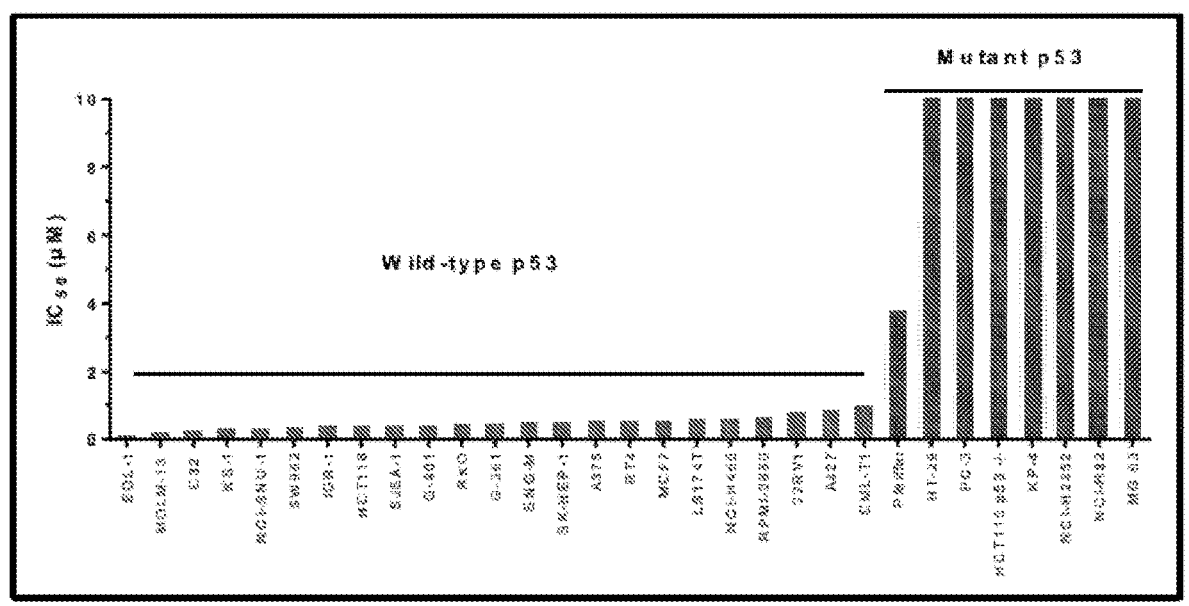
FIG. 2 illustrates that the compound of Formula (I) inhibits the proliferation of p53 WT tumor cells.

A broader panel of tumor cell lines was assayed, including both p53 wild-type (n=23) and mutant (n=7) lines representing a range of tumor types and genetic backgrounds, and determined the effect of the compound of Formula (I) treatment on cell growth over a 72-hour period. In the 23 p53 wild-type cell lines evaluated, the compound of Formula (I) treatment inhibited the growth of cells with IC50 values ranging from 0.1 to 1 mmol/L (FIG. 2).

Figure 4:
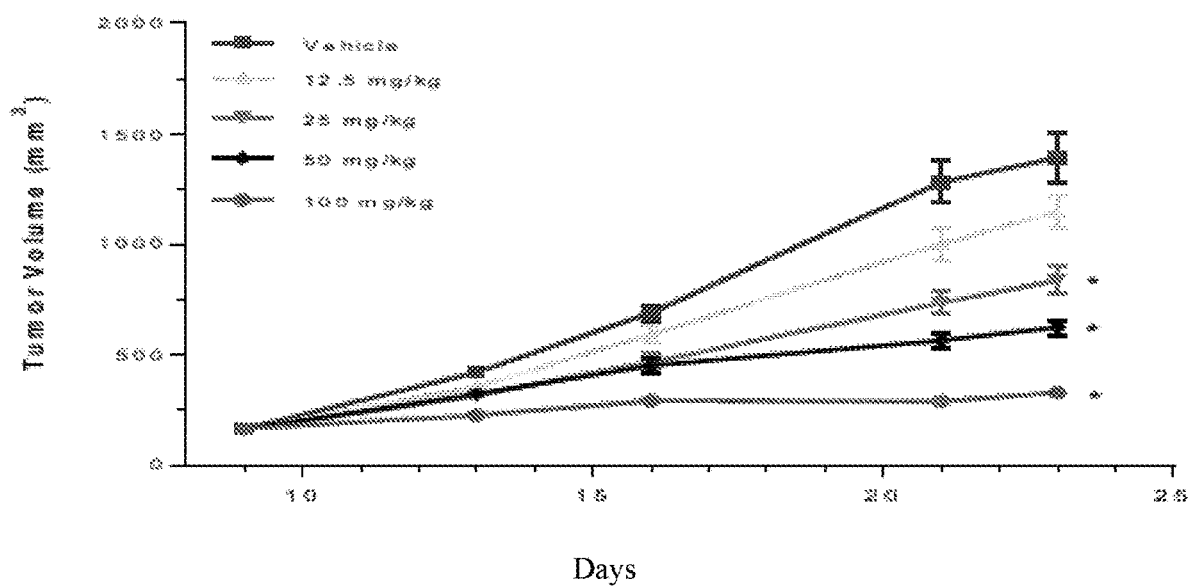
FIG. 4 illustrates that the compound of Formula (I) inhibits in vivo growth of the HCT116 (KRAS) tumor in a dose dependent manner. $ED_{50=31.6}$ mg/kg.
Figure 5:
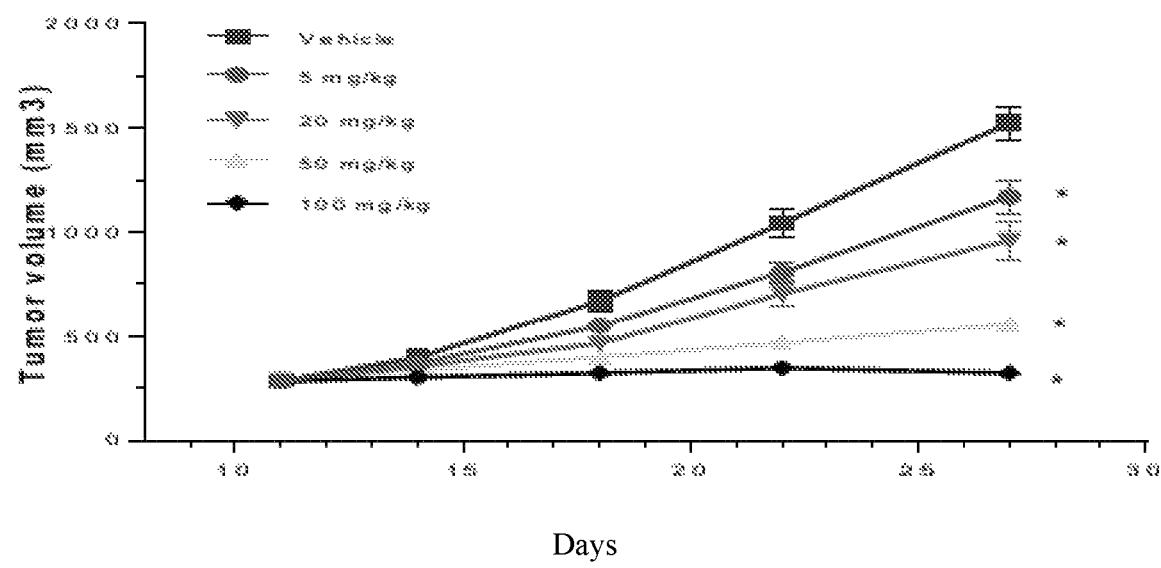
FIG. 5 illustrates that the compound of Formula (I) inhibits in vivo growth of the A375sq2 (BRAF) tumor in a dose dependent manner. $ED_{50=18}$ mg/kg.

The antitumor activity of the compound of Formula (I) was evaluated in xenograft models representing different genetic backgrounds and various tumor types. All tumor cell lines utilized in xenograft models harbored wild-type p53. Daily oral administration of the compound of Formula (I) resulted in significant tumor growth inhibition (TGI) across all models (FIGS. 3-5).

Figure 3:
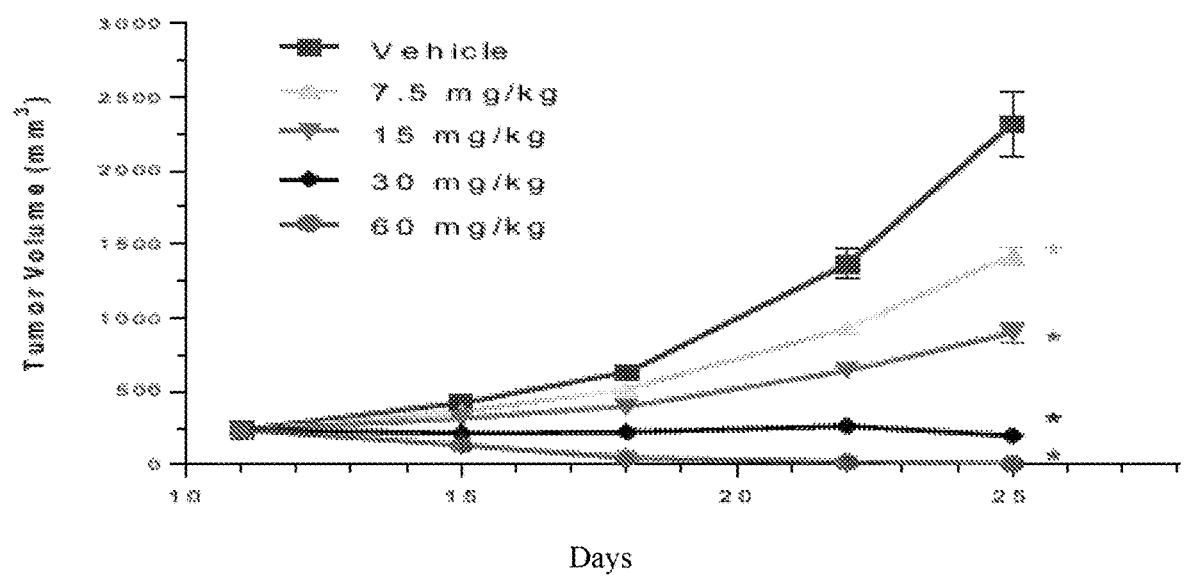
FIG. 3 illustrates that the compound of Formula (I) inhibits in vivo growth of the SJSA-1 (MDM2 amplified) tumor in a dose dependent manner. $ED_{50}=9.0$ mg/kg.

SJSA-1, an MDM2 amplified osteosarcoma model, was the most sensitive to the compound of Formula (I) treatment with an $ED_{50}$ of 9.1 mg/kg (FIG. 3). In the highest dose group of 75 mg/kg, 10 of 10 tumors completely regressed and were undetectable after 10 days of treatment. The compound of Formula (I) treatment was stopped in this group after day 25, and mice were observed for an additional 50 days. There was no detectable SJSA-1 tumor regrowth in any of the mice. Additional xenograft models demonstrated a range of in vivo antitumor activity of the compound of Formula (I) or Formula (II). In the HCT116 colorectal cancer model (KRAS mutant), the highest dose of the compound of Formula (I) resulted in 86% TGI compared with control, and the $ED_{50}$ was 31 mg/kg (FIG. 4). The compound of Formula (I) treatment in an A375sq2 BRAF-mutant melanoma model resulted in 97% TGI, with an $ED_{50}$ of 18 mg/kg (FIG. 5).

Figure 6:
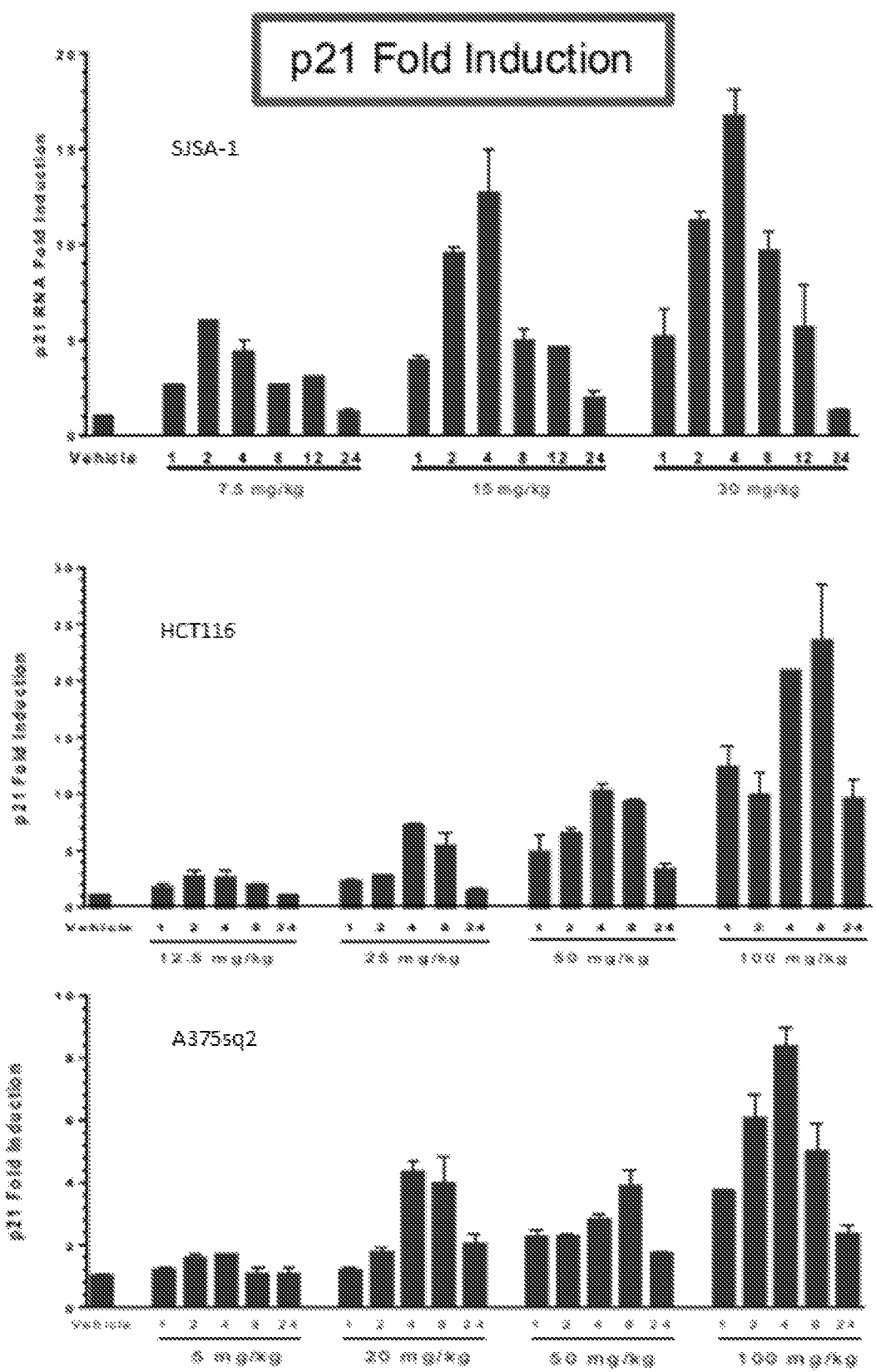
FIG. 6 illustrates the p21 fold induction of the compound of Formula (I) at different doses.
Figure 7:
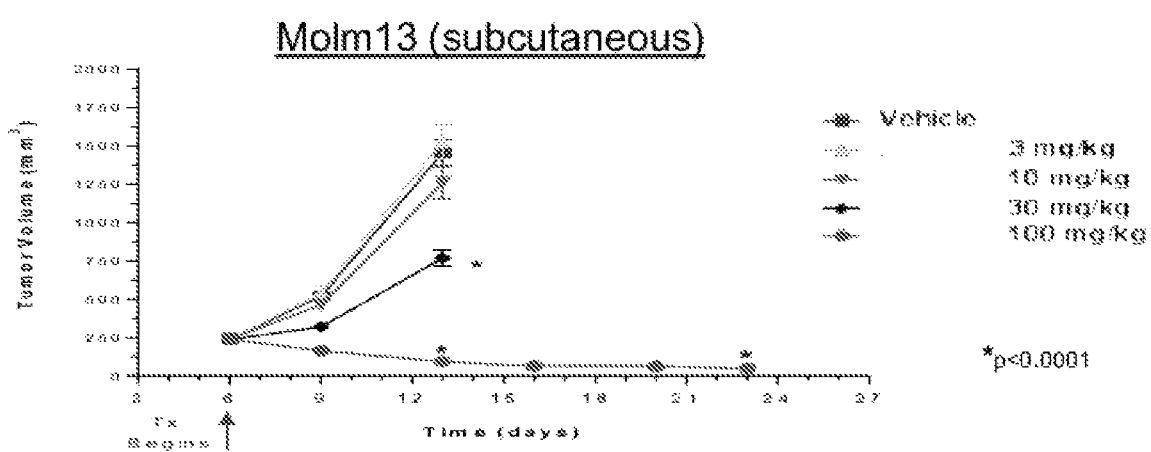
FIG. 7 illustrates that the compound of Formula (I) inhibits AML, tumor growth in a dose dependent manner.
Figure 8:
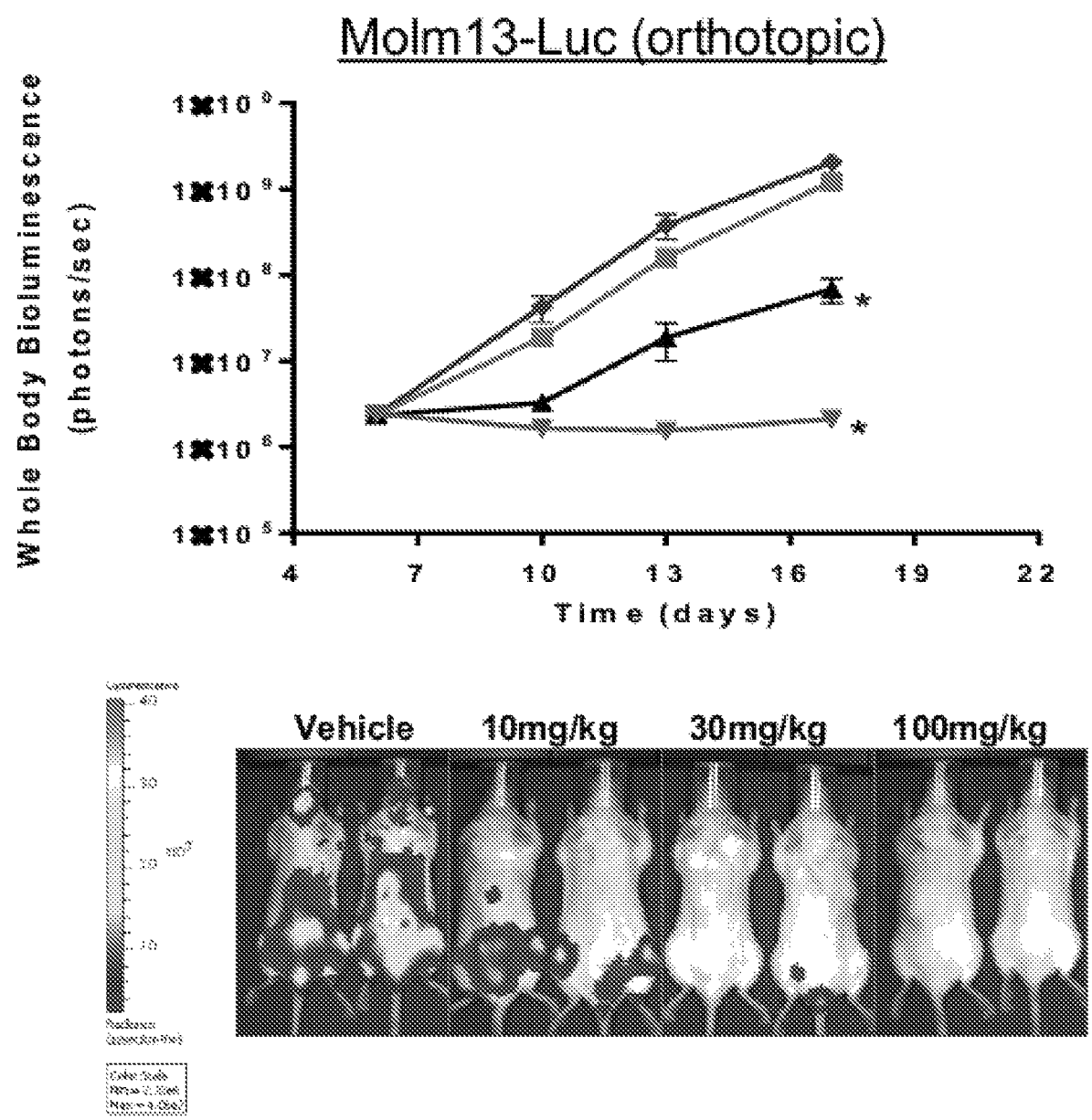
FIG. 8 illustrates that the compound of Formula (I) inhibits AML tumor growth in a mouse model in a dose dependent manner.
Figure 9:
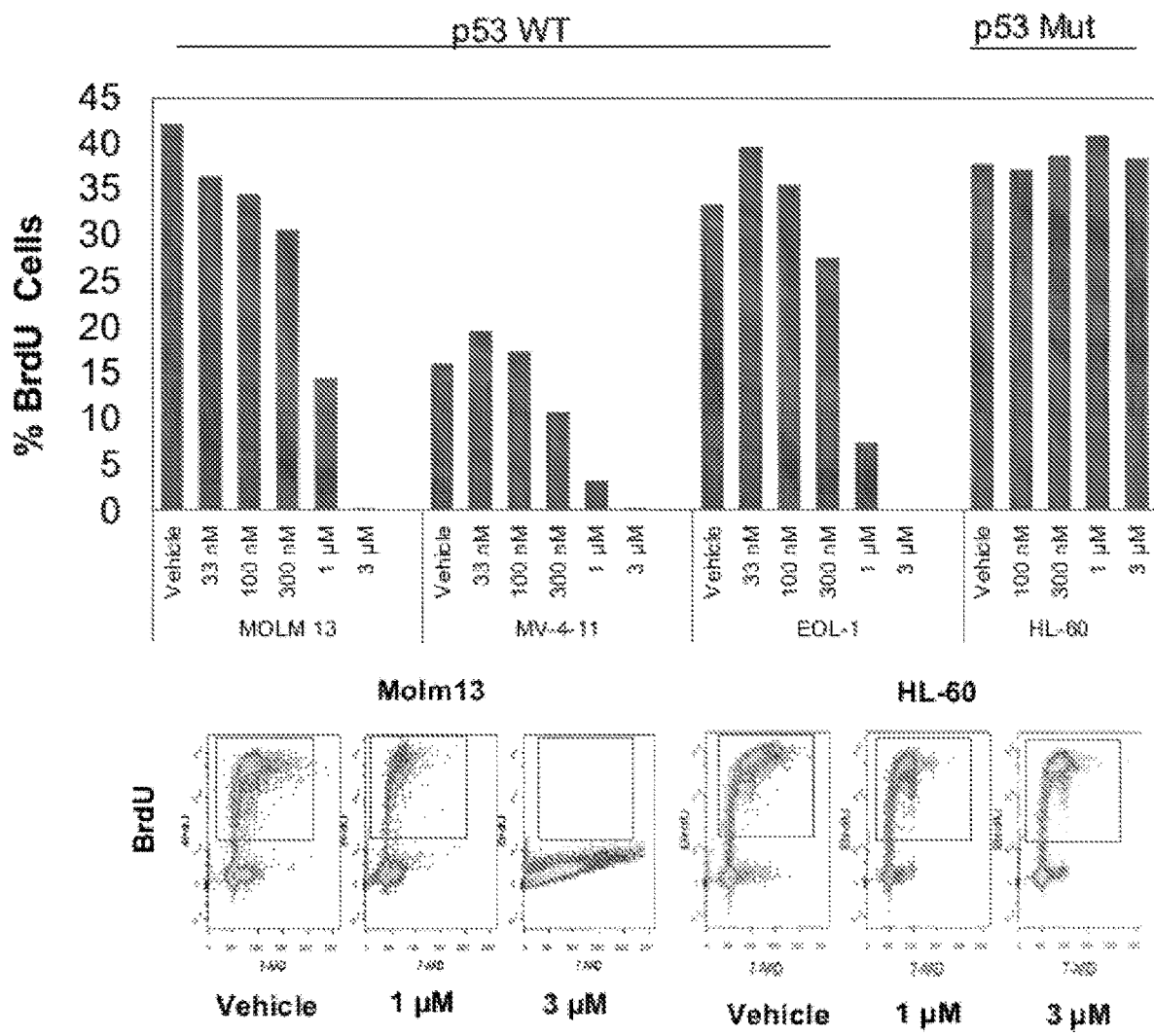
FIG. 9 illustrates that the compound of Formula (I) inhibits the cell cycle.
Figure 10:
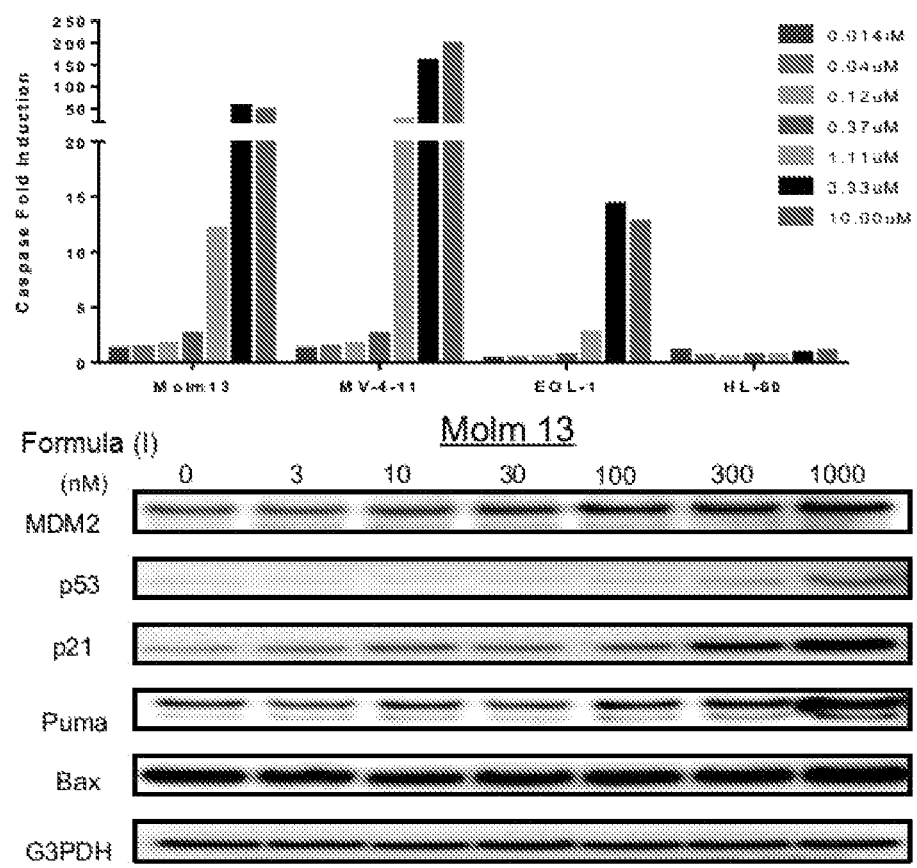
FIG. 10 illustrates that the compound of Formula (I) induces apoptosis in p53 wild type AML cell lines.

Tumors were harvested at the end of each xenograft study to determine the effect of the compound of Formula (I) treatment on p53 pathway activity. The compound of Formula (I) treatment resulted in a dose- and time-dependent induction of p21 mRNA compared with vehicle-treated tumors (FIG. 6). The level of p21 induction within each tumor model related to the degree of TGI, where p21 levels were highest in tumors whose growth was most inhibited. However, the maximum p21 induction level varied across tumor models.

Example 8

Clinical Trial

Two-Part, Randomized, Open-label, Multicenter, Phase 2a/2b Study of the Efficacy, Safety, Pharmacokinetics, and Pharmacodynamics of the Compound of Formula (I) Compared to Ruxolitinib in Patients with Phlebotomy-Dependent Polycythemia Vera.

Polycythemia Vera (PV) is classified as a myeloproliferative neoplasm (MPN). Long-term survival is poor, with a 18% survival rate after 20 years. Limited therapeutic options exist for PV patients, especially those who are hydroxyurea (HU) intolerant/resistant, and these patients are often treated with HU despite unacceptable side effects and unsatisfactory response. With ruxolitinib response rates at 21%, there is a high unmet need for efficacious treatments in this subset of PV patients. The compound of Formula (I) or Formula (II) is an orally bioavailable, small molecule, cytotoxic chemotherapeutic agent that binds to murine double minute chromosome 2 (MDM2) and inhibits the MDM2/tumor protein 53 (p53) protein-protein interaction. The compound of Formula (I) has been shown to inhibit the growth of p53 wild type (p53WT) tumor cells in vitro and tumor xenografts in vivo. p53 is a tumor suppressor and transcription factor that responds to cellular stress by activating the transcription of numerous genes involved in cell cycle arrest, apoptosis, senescence, and deoxyribonucleic acid (DNA) repair. Preclinically, the key determinant of sensitivity to MDM2 inhibition is the p53 mutational status of cells, with p53WT cells being sensitive to such inhibitors. MDM2 is a negative regulator of p53 and is overexpressed in CD34+ myeloproliferative neoplasm cells harboring p53WT. MDM2 degrades and inactivates p53, allowing clonal hematopoietic stem cells to proliferate.

Study Design

The study will be conducted in two parts. In Part A, an initial proof-of-concept phase, three treatment arms will be evaluated for efficacy and safety in subjects with PV. If the Overall Response Rate in Part A is at least 40% in subjects with splenomegaly, Part B will commence, whereby PV subjects with splenomegaly will be randomly assigned to treatment with either the recommended dose and schedule from Part A, or to ruxolitinib administered per the prescribing label.

All Part A and Part B subjects will continue the compound of Formula (I) treatment until disease progression or lack of tolerability. Disease progression is defined as:
  Phlebotomy Eligibility (after Week 8): A confirmed hematocrit (HCT)>45% that is at least 3 percentage points higher than the HCT obtained at baseline or a confirmed HCT>48%, with confirmation occurring 2 to 14 days subsequent to the initial observation.
  Spleen Progression: A volumetric assessment that is ≥25% increased relative to the volume determined at the time of the best documented spleen volume response by central imaging review.
  Bone Marrow Fibrosis/Transformation: Increased bone marrow fibrosis from baseline, and/or transformation to myelofibrosis (MF), myelodysplastic syndrome (MDS), or acute leukemia.

Part A—the compound of Formula (I) Proof-of-Concept/Dose Determination: Part A will evaluate the safety and efficacy of two different doses and two different schedules of the compound of Formula (I) in three treatment arms in subjects with PV. A total of 75 randomized subjects will be evaluated in Part A. Subjects will be randomly assigned to one of three treatment arms:
  Arm 1, N=15 with splenomegaly, plus N=10 without splenomegaly: 120 mg once daily for Days 1-7, off treatment for Days 8-21 (21-day cycle)

Arm 2, N=15 with splenomegaly, plus N=10 without splenomegaly: 240 mg once daily for Days 1-7, off treatment for Days 8-21 (21-day cycle)

Arm 3, N=15 with splenomegaly, plus N=10 without splenomegaly: 120 mg once daily for Days 1-7, off treatment for Days 8-28 (28-day cycle)

Part B—the compound of Formula (I) at Recommended Dose and Schedule from Part A vs. Ruxolitinib in Subjects with PV: A total of 220 randomized subjects with splenomegaly will be evaluated in Part B. Subjects in Part B will be randomly assigned to treatment with the recommended dose of the compound of Formula (I) and schedule determined by the DMC from Part A or to ruxolitinib per the prescribing label:

Arm 1, N=110: Subjects with splenomegaly will be treated with the compound of Formula (I) at the recommended dose and schedule from Part A Arm 2, N=110: Subjects with splenomegaly will be treated with ruxolitinib per the prescribing label.

Approximately 295 randomized subjects are planned: Part A: N=75 •Part B: N=220 (110 subjects receiving the compound of Formula (I) and 110 subjects receiving ruxolitinib)

Study Objectives:

| Part A Primary Objectives | Endpoint/Outcome Measure |
|---|---|
| To determine the efficacy of the compound of Formula (I) in PV subjects with splenomegaly who are phlebotomy dependent. The primary efficacy analysis for Part A will be based on the modified Intent-to Treat (mITT) analysis of only Part A subjects with splenomegaly that are p53WT. | Proportion of subjects with splenomegaly achieving a response at Week 32, with response defined as having achieved both of the following: The absence of phlebotomy eligibility beginning at the Week 8 visit and continuing through Week 32, with no more than one phlebotomy eligibility occurring postrandomization and prior to the Week 8 visit. A reduction in spleen volume as assessed by MRI (or CT) ≥35% from baseline at Week 32 |
| To determine the dose of the compound of Formula (I) in PV subjects with splenomegaly to be evaluated against ruxolitinib in Part B | Selection of the compound of Formula (I) dose in PV subjects with splenomegaly that has an overall response rate of >40% in Part A |

| Part B Primary Objective | Endpoint Outcome Measure |
|---|---|
| To demonstrate superiority of the compound of Formula (I) vs. ruxolitinib in PV subjects with splenomegaly who are resistant/intolerant to hydroxyurea | Proportion of subjects with splenomegaly achieving a response at Week 32, with response defined as having achieved both of the following: The absence of phlebotomy eligibility beginning at the Week 8 visit and continuing through Week 32, with no more than one phlebotomy eligibility occurring postrandomization and prior to the Week 8 visit A reduction in spleen volume as assessed by MRI (or CT) ≥35% from baseline at Week 32 |

Inclusion Criteria:
1. Adults >18 years of age.
2. Documentation that the patient has met the revised 2016 World Health Organization (WHO) criteria for the diagnosis of PV.
3. Subjects must be phlebotomy dependent. The definition of phlebotomy dependent is: •Hematocrit is 40-45% with two phlebotomies or more spaced at least 4 weeks apart within 24 weeks before Screening or•Hematocrit level is higher than 45% with at least one phlebotomy within 16 weeks before Screening.
4. In Part A, subjects with splenomegaly (defined as spleen volume ≥450 cubic centimeters cm3) and without splenomegaly by MRI (or CT) are eligible. In Part B, only subjects with splenomegaly by MRI or CT are eligible.
5. Previous treatment with hydroxyurea (HU) (Part A and B), or interferon (Part A only). If previously treated with HU, subject must be resistant to/intolerant of HU according to the following criteria:

HU resistance is defined as:
a dose ≥2 g/day or a maximum tolerated dose <2 g/day for a minimum of 12 weeks, resulting in need for phlebotomy to maintain hematocrit <45% or platelet count >400×10$^9$/L and white blood cell (WBC) count >10×10$^9$ /L.

HU intolerance is defined as:
ANC<1.0×10$^9$/L or platelet count <100×10$^9$/L or hemoglobin <100 g/L (i.e., 10 g/dL) at the lowest dose of HU required to achieve a response (hematocrit <45% without phlebotomy and/or all 3 of a platelet count ≤400×10$^9$/L, a WBC count ≤10× 10$^9$/L, and a nonpalpable spleen) or Presence of leg ulcers or other unacceptable HU-related nonhematologic toxicities (such as mucocutaneous manifestations, gastrointestinal symptoms, pneumonitis, or fever at any dose of HU), defined as: Common Terminology Criteria for Adverse Events (CTCAE) version 5.0 grade 3-4 adverse event (AE) or >1 week of CTCAE version 5.0 grade 2 AE or Permanent discontinuation of HU or Interruption of HU until toxicity resolved or Hospitalization due to HU toxicity.
6. Eastern Cooperative Oncology Group (ECOG) performance status of 0, 1, or 2.
7. Females of childbearing potential and males who have partners of childbearing potential must agree to use an effective contraception method during the study. In addition, males must continue to use contraception for 3 months after the last dose of study drug and females must continue to use contraception for 1 week after the last dose of study drug. Effective birth control includes (a) combined, estrogen and progestogen containing, hormonal contraception (oral, intravaginal, transdermal); (b) progestogen-only hormonal contraception (oral, injectable, implantable); (c) intrauterine device; (d) intrauterine hormone-releasing system; (e) bilateral tubal occlusion; (f) vasectomised partner; and (g) sexual abstinence.

Exclusion Criteria
1. Meets the criteria for post-PV myelofibrosis, as defined by the International Working Group-Myeloproliferative Neoplasms Research and Treatment (IWG-MRT).
2. >10% blasts.
3. Clinically significant thrombosis within 3 months of screening.
4. Inadequate liver or renal function:
    a. Renal impairment (estimated creatinine clearance <45 mL/min by Cockcroft Gault):

$$eC_{Cr} = \frac{(140 - \text{Age}) \times \text{Mass(in kilograms)} \times [0.85 \text{ if Female}]}{72 \times \text{Serum Creatinine (in mg/dL)}}.$$

b. Known history of hepatocellular disease (for example, hepatitis B or C, cirrhosis or other hepatocellular disease).
    c. Total bilirubin ≥2× upper limit of laboratory normal (ULN) unless Gilbert's Syndrome
    d. Alanine aminotransferase (ALT)>2.5× ULN.
5. Part B only: Previous treatment with a JAK inhibitor.
6. Previous treatment with histone deacetylase (HDAC) inhibitors or BCL-2 inhibitors.
7. Patients previously treated with MDM2 antagonist therapies, p53-directed therapies, or patients receiving interferon-alpha, anagrelide, or ruxolitinib within 28 days or approximately 5 half-lives, or hydroxyurea within 1 day, or subjects receiving any other cytoreductive or investigational agents within 28 days or 5 halflives of initial dose. Aspirin is permitted per treatment guidelines for PV unless medically contraindicated.
8. Absolute neutrophil count <1.5×10$^9$/L prior to dosing on Cycle 1 Day 1.
9. Platelet count ≤150×10$^9$/L prior to dosing on Cycle 1 Day 1.
10. Splenic radiation within 3 months prior to first dose of the compound of Formula (I).
11. Women who are pregnant or breastfeeding.
12. History of major organ transplant.
13. Uncontrolled intercurrent illness including, but not limited to, acute hepatitis A; known history of human immunodeficiency virus (HIV)-positive; clinically significant cardiac disease (New York Heart Association Class III or IV); symptomatic congestive heart failure; unstable angina pectoris; ventricular arrhythmia; or psychiatric illness/social situations that would limit compliance with study requirements.
14. Subjects with clinically significant bacterial, fungal, parasitic, or viral infection that requires therapy. Subjects with acute bacterial infections requiring antibiotic use should delay screening/enrollment until the course of antibiotic therapy has been completed.
15. Other malignancy within the last 3 years, other than curatively treated basal cell or squamous cell skin cancer, carcinoma in situ of the cervix, organ-confined or treated nonmetastatic prostate cancer with normal prostate-specific antigen, in situ breast carcinoma after complete surgical resection, or superficial transitional cell bladder carcinoma.
16. Grade 2 or higher QTc prolongation (>480 milliseconds, per NCI-CTCAE criteria, version 5.0).

Randomization Procedure

In Part A, subjects will be randomly assigned to one of three treatment arms. In Part B, subjects will be randomly assigned to the compound of Formula (I) or to ruxolitinib. Subjects in Part B only will be stratified on the basis of HU status: HU intolerance (unacceptable side effects) vs. HU resistance (inadequate response). Subjects will be categorized as HU resistant or intolerant at the Screening visit and this categorization will be used to enable subject stratification at randomization (Study Day 1).

Statistical Analysis

This study will be conducted in two parts. In Part A, an initial proof-of-concept phase, study subjects will be randomly assigned into 1 of 3 treatment arms: the compound of Formula (I) at 120 mg on a 21-day treatment cycle, the compound of Formula (I) at 240 mg on a 21-day treatment cycle, or the compound of Formula (I) at 120 mg on a 28-day treatment cycle. All three arms are conducted identically and will follow the same study assessments. The primary efficacy analysis for Part A will be based on the mITT analysis of only baseline splenomegaly subjects that are p53WT. After all subjects with baseline splenomegaly in Part A have had the opportunity to complete Week 32, the compound of Formula (I) dose/schedule for Part B will be recommended by the DMC. For Part B, subjects with baseline splenomegaly will be randomly assigned to treatment with either the recommended dose/schedule of the compound of Formula (I) from Part A, or to ruxolitinib administered per the prescribing label. Results of statistical analyses, descriptive summary statistics and supportive listings will be presented by study part (A or B), treatment arm, and dose. All analyses, summaries, and listings will be performed using SAS software (version 9.4 or higher). A detailed methodology for summary and statistical analysis of the data collected in this study will be documented in a Statistical Analysis Plan (SAP) that will be finalized prior to database lock. The SAP may modify the data analysis plans outlined in the protocol; and if so, will be clearly documented in the SAP. Any major modifications of the study design or study endpoints and/or its analysis will also be reflected in a protocol amendment.

Study Duration

The study will be considered complete 2 years after the last subject is enrolled, at which time subjects who remain on study treatment will be evaluated for eligibility to enroll in a rollover study.

Example 9

An Open-Label, Phase 2a/2b Study of the Compound of Formula (I) in Subjects with Primary Myelofibrosis (PMF), Post-Polycythemia Vera MF (Post-*PV-MF), or Post-Essential Thrombocythemia MF (Post-ET-MF) Who have Failed Ruxolitinib There is a significant unmet need for improved therapies in patients with myelofibrosis (MF) who have primary resistance to, suboptimal responses to, or who have relapsed after treatment with ruxolitinib. The compound of Formula (I) is an orally bioavailable, small molecule, cytotoxic chemotherapeutic agent that binds to murine double minute chromosome 2 (MDM2) and inhibits the MDM2/tumor protein 53 (p53) protein-protein interaction. The compound of Formula (I) has been shown to inhibit the growth of p53 wild type (p53WT) tumor cells in vitro and tumor xenografts in vivo. p53 is a tumor suppressor and transcription factor that responds to cellular stress by activating the transcription of numerous genes involved in cell cycle arrest, apoptosis, senescence, and deoxyribonucleic acid (DNA) repair. Preclinically, the key determinant of sensitivity to MDM2 inhibition is the p53 mutational status of cells, with p53WT cells being sensitive to such inhibitors. MDM2 is a negative regulator of p53 and is overexpressed in CD34+ myeloproliferative neoplasm cells harboring p53WT. MDM2 degrades and inactivates p53, allowing clonal hematopoietic stem cells to proliferate.

Study Design

This is an open-label, 2-part (Part A and Part B), Phase 2a/2b study of the compound of Formula (I) in subjects with PMF, post-PV-MF, or post-ET-MF who have failed ruxolitinib. Approximately 190 subjects will be enrolled in the study (90 in Part A and 100 in Part B).

Part A (N=90): In Part A of the study, subjects will be randomly assigned to 1 of 3 treatment groups:
- Cohort 1, N=30 subjects: The compound of Formula (I) at 120 mg once daily for Days 1-7, off treatment for Days 8-21 (21-day cycle)
- Cohort 2, N=30 subjects: The compound of Formula (I) at 240 mg once daily for Days 1-7, off treatment for Days 8-21 (21-day cycle)
- Cohort 3, N=30 subjects: The compound of Formula (I) at 240 mg once daily for Days 1-7, off treatment for Days 8-28 (28-day cycle)

Part B (N=100): Approximately 100 subjects will be enrolled into Part B and treated at the recommended dose and schedule from Part A. A Data Monitoring Committee (DMC) will convene every 3 months for Part A and Part B during the conduct of the study to review the safety data for the clinical study. The DMC will also convene after all subjects in Part A have had the opportunity to complete the Week 24 assessment. The DMC will determine the recommended dose and schedule of the compound of Formula (I) for Part B based on the efficacy and safety data from Part A. In Part A and Part B, subjects will receive the compound of Formula (I) orally (PO) QD on Days 1 to 7 of each 21-day or 28-day cycle. Dose reductions for hematologic and non-hematologic toxicity will be allowed. All subjects should be treated until disease progression or lack of tolerability. The definition of disease progression is based on imaging and modified ELN criteria:

Increase in splenic volume of ≥25% from on-study nadir by MRI (or CT) by central imaging review Leukemic transformation confirmed by a bone marrow blast count of ≥20% or A peripheral blood blast content of ≥20% associated with an absolute blast count of ≥1×10$^9$/L that lasts for at least 2 weeks.

Study Objectives

| Primary Objectives | Endpoint/Outcome Measure |
|---|---|
| To determine spleen response | The proportion of subjects achieving a >35% spleen volume reduction from Baseline to Week 24, as assessed by magnetic resonance imaging (MRI) or computed tomography (CT) scan |

Inclusion Criteria

Subjects in both Part A and Part B must meet all of the following criteria in order to be eligible for the study:

1. Adults >18 years of age.
2. Palpable splenomegaly at least 5 cm below left costal margin.
3. Confirmed diagnosis of PMF, post-PV-MF, or post-ET-MF, as assessed by treating physician according to the World Health Organization (WHO) criteria.
4. High-risk, intermediate-2 risk, or intermediate-1 risk, defined by Dynamic International Prognostic System (DIPSS).
5. ECOG performance status of 0 to 2.
6. Adequate hematological, hepatic, and renal organ function (as per protocol definition and within 14 days prior to the first dose of the compound of Formula (I))•Hematologic: ANC≥1.0×10$^9$/L in the absence of growth factors during the prior 7 days; platelet count ≥100×10$^9$/L; Peripheral blood blast count <10%.

Hepatic: total bilirubin ≤2.0 times the upper limit of normal (ULN), unless Gilbert's Syndrome; aspartate transaminase/serum glutamic oxaloacetic transaminase (AST/SGOT) and alanine transaminase/serum glutamic pyruvic transaminase (ALT/SGPT)≤2.5 ULN•Renal: estimated creatinine clearance >45 mL/min by Cockcroft Gault:

$$eC_{Cr} = \frac{(140 - \text{Age}) \times \text{Mass(in kilograms)} \times [0.85 \text{ if Female}]}{72 \times \text{Serum Creatinine (in mg/dL)}}.$$

7. Females of childbearing potential and males who have partners of childbearing potential must agree to use an effective contraception method during the study. In addition, males must continue to use contraception for 3 months after the last dose of study drug and females must continue to use contraception for 1 week after the last dose of study drug. Effective birth control includes (a) combined, estrogen and progestogen containing, hormonal contraception (oral, intravaginal, transdermal); (b) progestogen-only hormonal contraception (oral, injectable, implantable); (c) intrauterine device; (d) intrauterine hormonereleasing system; (e) bilateral tubal occlusion; (f) vasectomised partner; and (g) sexual abstinence.

Subjects in Part A must meet the following ruxolitinib treatment failure criteria in order to be eligible for the study:

Ruxolitinib treatment failure in Part A must meet either criterion (a) or (b) below:
a) Either a lack of spleen response defined as receiving at least 12 weeks of ruxolitinib treatment and having both of the following:

Persistent splenomegaly, by physical exam, that is palpable >5 cm below the lower costal margin (LCM)
and TSS of >10 on the MPN-SAF TSS 2.0 or patients with a single symptom score of >5 or two symptoms of >3, including only the symptoms of left upper quadrant pain, bone pain, itching, or night sweats.

b) Or progressive disease any time while on ruxolitinib treatment as defined by any one of the following:
Spleen volume increase by >25% from the nadir as assessed by MRI or CT•Appearance of new splenomegaly that is palpable at least 5 cm below the LCM
A ≥100% increase in palpable distance, below the LCM, for baseline splenomegaly of 5 to 10 cm
A ≥50% increase in palpable distance, below the LCM, for baseline splenomegaly of >10 cm.

Subjects in Part B must meet the following ruxolitinib treatment failure criteria in order to be eligible for the study:

Ruxolitinib treatment failure in Part B must meet either criterion (a) or (b) below:
a) Either a lack of spleen response defined as receiving at least 12 weeks of ruxolitinib treatment and having at least one of the following:
For subjects that have a MRI or CT to assess ruxolitinib treatment, failure to have a least ≥35% reduction in spleen volume
A Baseline splenomegaly prior to ruxolitinib treatment that is palpable at 5 to 10 cm, below the LCM, but remains palpable
A Baseline splenomegaly prior to ruxolitinib treatment that is palpable >10 cm, below the LCM, but does not decrease by at least 50%
A Baseline splenomegaly prior to ruxolitinib treatment that is palpable <5 cm, below the LCM, is not eligible to be considered as a ruxolitinib treatment failure.

b) Or progressive disease any time while on ruxolitinib treatment as defined by any one of the following:
Spleen volume increase by ≥25% from the nadir as assessed by MRI or CT
Appearance of new splenomegaly that is palpable at least 5 cm below the LCM
A ≥100% increase in palpable distance, below the LCM, for baseline splenomegaly of 5 to 10 cm
A ≥50% increase in palpable distance, below the LCM, for baseline splenomegaly of >10 cm.

Exclusion Criteria

Subjects in both Part A and Part B who meet any of the following criteria will not be eligible for the study:
1. Participation in another interventional clinical trial within the past 4 weeks of the first dose of the compound of Formula (I) (participation in observational studies is permitted).
2. Recent/concurrent treatment such as a major surgery, chemotherapy, immunomodulating therapy, biologic therapy, radiation therapy, or investigational therapy within 4 weeks or approximately 5 half lives of the first dose of the compound of Formula (I).
3. Prior splenectomy.
4. Splenic irradiation within 3 months prior to the first dose of the compound of Formula (I).
5. Prior allogeneic stem-cell transplantation or eligible for allogeneic stem cell transplantation.
6. Prior treatment with histone deacetylase (HDAC) inhibitors or BCL-2 inhibitors.
7. Prior MDM2 inhibitor therapy or p53-directed therapy.
8. Women who are pregnant or breastfeeding.
9. History of major organ transplant.
10. Uncontrolled intercurrent illness including, but not limited to, acute hepatitis A; known history of human immunodeficiency virus (HIV)-positive; clinically significant cardiac disease (New York Heart Association Class III or IV); symptomatic congestive heart failure; unstable angina pectoris ventricular arrhythmia; or psychiatric illness/social situations that would limit compliance with study requirements.
11. Subjects with clinically significant bacterial, fungal, parasitic, or viral infection that requires therapy. Subjects with acute bacterial infections requiring antibiotic use should delay screening/enrollment until the course of antibiotic therapy has been completed.
12. Other malignancy within the last 3 years, other than curatively treated basal cell or squamous cell skin cancer, carcinoma in situ of the cervix, organconfined or treated nonmetastatic prostate cancer with normal prostate-specific antigen, in situ breast carcinoma after complete surgical resection, or superficial transitional cell bladder carcinoma.
13. Grade 2 or higher QTc prolongation (>480 milliseconds per NCI-CTCAE criteria, version 5.0).
14. Hematopoietic growth factors (i.e., erythropoietin (Epo), granulocyte colony stimulating factor (GCSF), romiplostim) within 28 days prior to receiving the first dose of the compound of Formula (I).
15. Active or chronic bleeding within 4 weeks prior to the first dose of the compound of Formula (I).

Randomization Procedure

Part A: Subjects will be randomized in a 1:1:1 allocation scheme to one of three treatment cohorts. A contract clinical service provider will develop the Part A randomization schedule and the actual randomization assignment will be made through a secure Interactive Response Technology (IRT) system. Part B: Subjects will be randomized to the the compound of Formula (I) dose and schedule recommended by the DMC.

Statistical Analysis

The DMC will convene every 3 months for Part A and Part B during the conduct of the study to review the safety data for the clinical study. The DMC will also convene after all subjects in Part A have had the opportunity to complete the Week 24 assessment. The DMC will determine the recommended dose and schedule of the compound of Formula (I) for Part B based on the efficacy and safety data from Part A. Results of statistical analyses, descriptive summary statistics, and supportive listings will be presented by study part (A or B) and within Part A (by cohorts).

Study Duration

The study will be considered complete 2 years after the last subject is enrolled, at which time subjects who remain on study treatment will be evaluated for eligibility to enroll in a rollover study.

Example 10

Effect of the Compound of Formula (I) on MPN-BP Stem Cells MPN-BP Cell Preparation Currently, $CD3^+$ cell-depleted mononuclear cells (MNC) from 1 patient with MPN-BP who had WT TP53 gene have been shown to be capable of serially engrafting and causing leukemia in NSG mice. In order to harvest sufficient cells to assess the effects of the compound of Formula (I) on MPN-BP stem cells, MPN-BP cells collected from the bone morrow (BM) or spleens of NSG mice will be passaged in NSG mice by serial transplantation. The mutational patterns and karyotypic abnormalities present in the cells following serial transplantation will be determined by capture based next generation sequencing (NGS) and fluorescence in situ hybridization (FISH).

Effect of the Compound of Formula (I) on MPN-BP Stem Cells

In order to examine the effects of the compound of Formula (I) on MPN-BP stem cells, 0.5-2×10⁶ cells/mouse harvested from NSG mice receiving MPN-BP cells will be transplanted into sublethally irradiated (220 cGy) 8-9-week-old NSG mice. The mice will then be monitored daily for their general condition and their body weight measured weekly. Twenty-eight days after transplantation, peripheral blood from the recipient mice will be collected and analyzed with the performance of complete blood counts (CBC) and flow cytometric analysis to determine if human MPN-BP has developed in these mice. These mice will be used in the following studies.

High Dose Study of the Compound of Formula (I)

The mice that have developed MPN-BP and have a similar leukemic burden in peripheral blood will be randomly divided into 2 groups of 3-4 mice. These two groups of mice will be treated with vehicle or the compound of Formula (I) (high dose, either 100 or 150 mg/kg) by oral gavage once per day for 7 days. After the treatment, peripheral blood blast count will be monitored using flow cytometric analysis weekly. Tolerability to the treatment will be assessed by daily body weight (BW) measurements. These analyses will allow to establish dynamics of MPN-BP return following each drug treatment which will be used to determine the treatment-free interval for the following survival and combination treatment studies.

Survival Study of the Compound of Formula (I)

The mice that have developed MPN-BP and have a similar leukemic burden in peripheral blood will be randomly divided into 3 groups of 4-5 mice and will be treated with the compound of Formula (I) by oral gavage at high dose (100 or 150 mg/kg) and low dose (30-50 mg/kg) once per day for 7 days. These cycles will be repeated for up to 3 cycles. After treatment, overall survival condition and the degree of disease progression will be monitored with blood counts and flow cytometric analysis of mouse blood every 14 days. The mice will be sacrificed if any of the following criteria are met: display of disease symptoms such as greater than 20% body weight loss, hunch-back, decreased activity; palpable splenomegaly extending across the midline; severe anemia, thrombocytopenia or leukopenia. The mice will be followed until they meet criteria for sacrifice. In addition, 2-3 mice receiving high or low dose of the compound of Formula (I) will be sacrificed after they complete 3 cycles of treatment even if they don't exhibit disease symptoms.

After the mice are sacrificed, cells will be recovered from the BM, spleen, and the peripheral blood and the presence of human CD45⁺, CD34⁺, CD33⁺, CD14⁺, Gly A⁺, CD41a⁺, CD19⁺, and CD3⁺ cells in these organs will be determined by mAb staining and flow cytometric analysis. These analyses will allow to determine whether the compound of Formula (I) treatment leads to improved survival and a reduction in the leukemic cell burden in mouse BM and a reduction in leukemic cell dissemination to the mouse spleen and peripheral blood. The remaining BMCs and spleen cells after flow cytometric analysis will be cryopreserved for quantification of the burden of MPN-BP cells and for assessment of the on-target effects of the compound of Formula (I). The hCD33⁺ cells in the BM of the recipient mice will be selected using a FACSAria cell sorter (BD) and will be analyzed using FISH for marker chromosomal abnormalities as well as variant allele frequencies of mutated myeloid malignancy genes.

I claim:

1. A method of treating a myeloproliferative neoplasm (MPN) comprising the step of administering to a human subject in need thereof a therapeutically effective amount of a MDM2 inhibitor, wherein the MDM2 inhibitor is a compound of Formula (I):

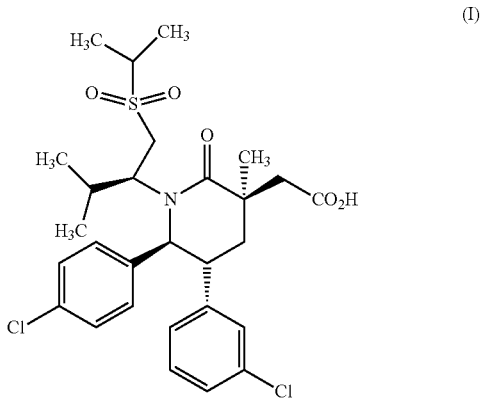

or a pharmaceutically acceptable salt thereof.

2. The method of claim 1, wherein the MPN is polycythemia vera (PV).

3. The method of claim 2, wherein the MPN is phlebotomy-dependent polycythemia vera.

4. The method of claim 1, wherein the MPN is thrombocythemia.

5. The method of claim 4, wherein thrombocythemia is essential thrombocythemia (ET).

6. The method of claim 1, wherein the MPN is myelofibrosis.

7. The method of claim 6, wherein myelofibrosis is selected from primary myelofibrosis (PMF), post-polycythemia vera myelofibrosis (post-PV MF), and post-essential thrombocythemia myelofibrosis (post-ET MF).

8. The method of claim 7, wherein the human subject did not respond to prior Ruxolitinib therapy.

9. The method of claim 1, wherein the MPN is systemic mastocystosis (SM).

10. The method of claim 1, wherein the MPN is chronic neutrophilic leukemia (CNL).

11. The method of claim 1, wherein the MPN is myelodysplastic syndrome (MDS).

12. The method of claim 1, wherein the MPN is systemic mast cell disease (SMCD).

13. The method of claim 1, wherein the MPN is chronic eosinophilic leukemia.

14. The method of claim 1, wherein the MPN is chronic myelomonocytic leukemia (CMML).

15. The method of claim 1, wherein the MPN is atypical chronic myeloid leukemia (aCML).

16. The method of claim 1, wherein the MPN is juvenile myelomonocytic leukemia (JMML).

17. The method of claim 1, wherein the MPN is hypereosinophilic syndromes (HES).

18. The method of claim 1, wherein the MPN is myelodysplastic/myeloproliferative neoplasms with ring sideroblasts and thrombocytosis (MDS/MPN-RS-T).

19. The method of claim 1, wherein the compound of Formula (I) is administered once daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

20. The method of claim 1, wherein the compound of Formula (I) is administered twice daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

21. The method of claim 1, wherein the human is treated with the MDM2 inhibitor on days 1-7 of 21-day cycle, wherein on days 8-21 the human is not treated with the MDM2 inhibitor.

22. The method of claim 1, wherein the compound of Formula (I) is orally administered.

23. The method of claim 1, wherein the therapeutically effective amount of the MDM2 inhibitor is 120 mg.

24. The method of claim 1, wherein the MPN is characterized by JAK2V617F mutation.

\* \* \* \* \*